US008815227B2

(12) United States Patent
McManus et al.

(10) Patent No.: US 8,815,227 B2
(45) Date of Patent: Aug. 26, 2014

(54) HYDROXYAPATITE-TARGETING MULTIARM POLYMERS AND CONJUGATES MADE THEREFROM

(71) Applicant: Nektar Therapeutics, San Francisco, CA (US)

(72) Inventors: Samuel P. McManus, Guntersville, AL (US); Antoni Kozlowski, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 13/865,021

(22) Filed: Apr. 17, 2013

(65) Prior Publication Data

US 2013/0331549 A1 Dec. 12, 2013

Related U.S. Application Data

(63) Continuation of application No. 12/738,980, filed as application No. PCT/US2008/012091 on Oct. 23, 2008, now Pat. No. 8,440,787.

(60) Provisional application No. 60/982,012, filed on Oct. 23, 2007.

(51) Int. Cl.
A61K 31/00 (2006.01)

(52) U.S. Cl.
USPC ........... 424/78.26; 424/78.08; 424/78.19; 424/78.22; 424/78.24; 424/78.37; 424/78.38; 514/75; 514/102; 514/109; 514/119; 523/115

(58) Field of Classification Search
None
See application file for complete search history.

(56) References Cited

U.S. PATENT DOCUMENTS

| 4,440,738 A | 4/1984 | Fawzi et al. |
|---|---|---|
| 4,642,229 A | 2/1987 | Cummings et al. |
| 4,670,417 A | 6/1987 | Iwasaki et al. |
| 4,760,057 A | 7/1988 | Alexander |
| 4,935,465 A | 6/1990 | Garman |
| 5,252,714 A | 10/1993 | Harris et al. |
| 5,281,698 A | 1/1994 | Nitecki |
| 5,286,637 A | 2/1994 | Veronese et al. |
| 5,412,072 A | 5/1995 | Sakurai et al. |
| 5,413,992 A | 5/1995 | Nicolaou et al. |
| 5,468,478 A | 11/1995 | Saifer et al. |
| 5,561,119 A | 10/1996 | Jacquesy et al. |
| 5,629,384 A | 5/1997 | Veronese et al. |
| 5,650,234 A | 7/1997 | Dolence et al. |
| 5,672,662 A | 9/1997 | Harris et al. |
| 5,766,618 A | 6/1998 | Laurencin et al. |
| 5,824,784 A | 10/1998 | Kinstler et al. |
| 5,840,900 A | 11/1998 | Greenwald et al. |
| 5,880,131 A | 3/1999 | Greenwald et al. |
| 5,900,461 A | 5/1999 | Harris |
| 5,932,462 A | 8/1999 | Harris et al. |
| 5,955,100 A | 9/1999 | Bosslet et al. |
| 6,103,236 A | 8/2000 | Suzawa et al. |
| 6,146,658 A | 11/2000 | Bosslet et al. |
| 6,342,244 B1 | 1/2002 | Zalipsky |
| 6,436,386 B1 * | 8/2002 | Roberts et al. ............. 424/78.17 |
| 6,677,320 B2 | 1/2004 | Diederich et al. |
| 6,750,340 B2 | 6/2004 | Padioukova et al. |
| 6,838,528 B2 | 1/2005 | Zhao |
| 7,589,157 B2 | 9/2009 | Zhao |
| 8,071,692 B2 | 12/2011 | Zhao |
| 8,440,787 B2 | 5/2013 | McManus et al. |
| 2004/0023852 A1* | 2/2004 | Roberts et al. .................... 514/7 |
| 2004/0170595 A1 | 9/2004 | Zhao |
| 2005/0054816 A1 | 3/2005 | McManus et al. |
| 2005/0170508 A1 | 8/2005 | Huang et al. |
| 2005/0287114 A1 | 12/2005 | Wang et al. |
| 2013/0331549 A1 | 12/2013 | McManus et al. |

FOREIGN PATENT DOCUMENTS

| EP | 0 512 844 | 11/1992 |
|---|---|---|
| JP | 02268190 | 11/1990 |
| WO | WO 92/20371 | 11/1992 |
| WO | WO 96/23794 | 8/1996 |
| WO | WO 98/00438 | 1/1998 |
| WO | WO 02/40058 | 5/2002 |
| WO | WO 03/000777 | 1/2003 |
| WO | WO 2006/050959 | 5/2006 |

OTHER PUBLICATIONS

Abuchowski, et al., "Cancer Therapy with Chemically Modified Enzymes. I. Antitumor Properties of Polyethylene Glycol-Asparaginase Conjugates," Cancer Biochem. Biophys., pp. 175-186, (1984).

Andresz, et al., "Chemische Sythese verzweigter Polysaccharide, 5* (Summary in English)," Makromol. Chem., vol. 179, pp. 301-312, (1978).

Beauchamp, et al., "A New Procedure for the Synthesis of Polyethylene Glycol-Protein Adducts; Effects on Function, Receptor Recognition, and Clearance of Superoxide Dismutase, Lactoferrin, and alpha2-Macroglobulin," Analy. Biochem., vol. 131, pp. 25-33, (1983).

Buckmann, et al., "Functionalization of Poly(ethylene glycol) and Monomethoxy-Poly(ethylene glycol)," Makromol. Chem., vol. 182, pp. 1379-1384, (1981).

Choi, et al., "Design of surface-modified poly(D,L-lactide-co-glycolide) nanoparticles for targeted drug delivery to bone," J. of Contrl. Rel., vol. 122, pp. 24-30, (2007).

Elling, et al., "Immunoaffinity Partitioning: Synthesis and Use of Polyethylene Glycol-Oxirane for Coupling to Bovine Serum Albumin and Monoclonal Antibodies," Biotech. and Appl. Biochem., vol. 13, pp. 354-362, (1991).

(Continued)

*Primary Examiner* — Marc Zimmer
(74) *Attorney, Agent, or Firm* — Timothy A. Marquart

(57) ABSTRACT

The present invention provides, among other things, polymeric reagents suitable for reaction with biologically active agents to form conjugates, the polymeric reagents comprising one or more polymer chains and a plurality of hydroxyapatite-targeting moieties, and optionally the reagents include one or more degradable linkages that serve to divide the polymer chains into polymer segments having a molecular weight suitable for renal clearance.

21 Claims, No Drawings

(56) References Cited

OTHER PUBLICATIONS

Goff, et al., "Substituted 2-Iminothiolanes: Reagents for the Preparation of Disulfide Cross-Linked Conjugates with Increased Stability," Bioconj. Chem., vol. 1, pp. 381-386, (1990).
Goodson, et al., "Site-Directed Pegylation of Recombinant Interleukin-2 at its Glycosylation Site," Bio/Tech., vol. 8, pp. 343-346, (Apr. 1990).
Guiotto, et al., "Anchimeric assistance effect on regioselective hydrolysis of branched PEGs: a mechanistic investigation," Bioorgan. & Med. Chem., vol. 12, pp. 5031-5037, (2004).
Greenwald, et al., "Effective drug delivery by PEGylated drug conjugates," Adv. Drug Del. Rel., vol. 55, pp. 217-250, (2003).
Harris, et al., "Effect of Pegylation on Pharmaceuticals," Nature, vol. 2, pp. 214-221, (Mar. 2003).
Harris, et al., "Synthesis and Characterization of Poly(ethylene Glycol) Derivatives," J. of Poly. Sci., vol. 22, pp. 341-352, (1984).
Hengst, et al., "Bone targeting potential of bisphosphonate-targeted liposomes Preparation, characterization and hydroxyapatite binding in vitro," Int. J. of Pharma., vol. 331, pp. 224-227, (2007).
Huang, et al., "A Polyethylene Glycol Copolymer for Carrying and Releasing Multiple Copies of Cysteine-Containing Peptides," Bioconj. Chem., vol. 9, pp. 612-617, (1998).
Joppich, et al., "Peptides Flanked by Two Polymer Chains, 1. Synthesis of Glycly-L-tryptophylglycine Substituted by Poly(ethylene oxide) at both the Carboxy and the Amino End Groups," Makromol. Chem., vol. 180, pp. 1381-1384, (1979).
Kogan, "The Synthesis of Substituted Methoxy-Poly(Ethylene Glycol) Derivatives Suitable for Selective Protein Modification," Syn. Commun., vol. 22, No. 16, pp. 2417-2424, (1992).
Li, "Poly(L-glutamic acid)-anticancer drug conjugates," Adv. Drug Del. Rel., vol. 54, pp. 695-713, (2002).
Modi, et al., "Clearance of pegylated (40KDA) interferon alfa-2A-(Pegasys®) is primarily hepatic," Hepatology, vol. 32, No. 4, Pt. 2, pp. 371A (848), (2000).
Ouchi, et al., "Design of Antitumor Agent-Terminated Poly(Ethylene Glycol) Conjugate as Macromolecular Prodrug," Polymer Preprints, vol. 38, No. 1, pp. 582-583, (1997).
Olson, et al., "Preparation and Characterization of Poly(ethylene glycol)ylated Human Growth Hormone Antagonist," Amer. Chem. Soc., pp. 170-181, (1997).
Pitha, et al., "Detergents Linked to Polysaccharides: Preparation and Effects on Membranes and Cells," Eur. J. Biochem., vol. 94, pp. 11-18, (1979).
Reddy, et al., "Use of peginterferon alfa-2a (40 KD) (Pegasys®) for the treatment of hepatitis C," Adv. Drug Del. Rev., vol. 54, pp. 571-586, (2002).
Romani, et al., "Synthesis of Unsymmetrical Cystine Peptides: Directed Disulfide Pairing with the Sulfenohydrazide Method," Chem. of Pep. and Proteins, vol. 2, pp. 29-34, (1984).
Sartore, et al., "Enzyme Modification by MPEG with an Amino Acid or Peptide as Spacer Arms," Appl. Biochem. and Biotech., vol. 27, pp. 45-54, (1991).
Sawhney, et al., "Bioerodible Hydrogels Based on Photopolymerized Poly(ethylene glycol)-co-poly(alpha-hydroxy acid) Diacrylate Macromers," Macromol., vol. 26, pp. 581-587, (1993).
Suzawa, et al., "Synthesis and HPLC analysis of enzymatically cleavable linker consisting of poly(ethylene glycol) and dipeptide for the development of immunoconjugate," J.of Contrl. Rel., vol. 69, pp. 27-41, (2000).
Suzawa, et al., "Synthesis of a Novel Duocarmycin Derivative DU-257 and its Application to Immunoconjugate Using Poly(ethylene glycol)-dipeptidyl Linker Capable of Tumor Specific Activation," Bioorgan. & Med. Chem., vol. 8, pp. 2175-2184, (2000).
Tondelli, et al., "Poly(ethylene glycol) Imidazolyl Formates as Oligomeric Drug-Binding Matrices," J. of Contrl. Rel., vol. 1, pp. 251-257, (1985).
Ulbrich, et al., "Poly(ethylene glycol)s containing enzymatically degradable bonds," Makromol. Chem., vol. 187, pp. 1131-1144, (1986).
Uludag, "Bisphosphonates as a Foundation of Drug Delivery to Bone," Curr. Pharma. Des., vol. 8, pp. 1929-1944, (2002).
Veronese, et al., "Surface Modification of Proteins. Activation of Monomethoxy-Polyethylene Glycols by Phenylchloroformates . . . ," Appl. Biochem. and Biotech., vol. 11, pp. 141-152, (1985).
Wang, et al., "Synthesis and Evaluation of Water-Soluble Polymeric Bone-Targeted Drug Delivery Systems," Bioconj. Chem., vol. 14, pp. 853-859, (2003).
Woghiren, et al., "Protected Thiol-Polyethylene Glycol: A New Activated Polymer for Reversible Protein Modification," Bioconj. Chem., vol. 4, pp. 314-318, (1993).
Zalipsky, et al., "Attachment of Drugs to Polyethylene Glycols." Eur. Polym. J., vol. 19, No. 12, pp. 1177-1183, (1983).
Zalipsky, et al., "New Detachable Poly(ethylene glycol) Conjugates: Cysteine-Cleavable Lipopolymers Regenerating Natural Phospholipid, Diacyl Phosphatidylethanolamine," Amer. Chem. Soc., vol. 10, No. 5, pp. 703-707, (Sep./Oct. 1999).
Zhang, et al., "The Interaction of Cationic Polymers and Their Bisphosphonate Derivatives with Hydroxyapatite," Macromol. Biosci., vol. 7, pp. 656-670, (2007).
PCT International Search Report corresponding to PCT Application No. PCT/US2008/012091 date of mailing Oct. 7, 2009.
PCT International Preliminary Report on Patentability corresponding to PCT Application No. PCT/US2008/012091, date of mailing May 6, 2010.
Enzon Pharmaceuticals, Macromolecular Engineering Technologies, pp. 1-14, (2004).
Nektar™—Transforming Therapeutics, Nektar Molecule Engineering: Polyethylene Glycol and Derivatives for Advanced PEGylation, pp. 1-20, Catalog—2003, (Jul. 2003).
Nektar™—Transforming Therapeutics, Nektar Advanced PEGylation: Polyethylene Glycol and Derivatives for Advanced PEGylation, pp. 1-24, Catalog—2004, (Jul. 2004).
Nektar™—Transforming Therapeutics, Nektar Advanced PEGylation: Polyethylene Glycol and Derivatives for Advanced PEGylation, pp. 1-30, (Catalog 2005-2006).
NOF Corporation, "PEG Derivatives, Phospholipid and Drug Delivery Materials for Pharmaceuticals", pp. 1-46, Catalogue 2003-1st, (Jan. 2003).
NOF Corporation, "PEG Derivatives, Phospholipid and Drug Delivery Materials for Pharmaceuticals", pp. 1-50, Catalogue 2003-2nd, (Mar. 2004).
NOF Corporation, "PEG Derivatives, Phospholipids and Drug Delivery Materials for Pharmaceutical Products and Formulations", pp. 1-59, Catalogue Ver. 8, (Apr. 2006).
Polypure, Products; PEG amines; PEG acids and amino acids; PEG thiols and disulfides; Biotins, (Apr. 2004).
Polypure, Products; PEG amines; PEG acids and amino acids; PEG thiols and disulfides; Biotins, (Apr. 2005).
Quanta Biodesign, Labeling, Derivatization and Crosslinking Reagents for Biological and Related Materials with dPEG™, pp. 1-38, (Mar. 12, 2004).
Quanta Biodesign, Labeling, Modification and Crosslinking Reagents incorporating our unique monodispersed dPEG™ Technology, pp. 1-31, (Nov. 5, 2004).
Quanta Biodesign, Ltd., Leading innovator, producer and provider of monodisperse discrete PEG™ (dPEG™) derivatives, (Product Catalog), pp. 1-51, (Updated: Jul. 18, 2005).
Quanta Biodesign, Ltd., Leading innovator, producer and provider of monodisperse discrete PEG™ (dPEG™) derivatives, (Product Catalog), pp. 1-51, (Updated: Nov. 17, 2005).
Shearwater Polymers, Inc., Polyethylene Glycol and Derivatives, pp. 1-49, (Catalog—Mar. 1995).
Shearwater Polymers, Inc., Polyethylene Glycol and Derivatives, pp. 1-53, (Catalog—Jul. 1997).
Shearwater Polymers, Inc., Polyethylene Glycol and Derivatives: Functionalized Biocompatible Polymers for Research and Pharmaceuticals, pp. 1-50, (Catalog—Jan. 2000).
Shearwater Corporation, Polyethylene Glycol and Derivatives for Biomedical Applications, pp. 1-17, (Catalog—Jul. 2001).
Australian Patent Examination Report No. 1 corresponding to Australian Patent Application No. 2008317383 date of issue Sep. 28, 2012.

(56) References Cited

OTHER PUBLICATIONS

Chinese Notification of the First Office Action corresponding to Chinese Patent Application No. 200880112961.4 dated Jul. 1, 2011.
Chinese Notification of the Second Office Action corresponding to Chinese Patent Application No. 200880112961.4 dated Jul. 5, 2012.
Chinese Notification of the Third Office Action corresponding to Chinese Patent Application No. 200880112961.4 dated Feb. 22, 2013.
Chinese Rejection Decision corresponding to Chinese Patent Application No. 200880112961.4 dated Oct. 9, 2013.
Japanese Notice of Reasons for Rejection corresponding to Japanese Patent Application No. 2010-531043 mailed Apr. 2, 2013.
Mexican Office Action corresponding to Mexican Patent Application No. MX/A/2010/004400 dated May 20, 2013.
Mexican Office Action corresponding to Mexican Patent Application No. MX/A/2010/004400 dated Aug. 26, 2013.

* cited by examiner

HYDROXYAPATITE-TARGETING MULTIARM POLYMERS AND CONJUGATES MADE THEREFROM

CROSS REFERENCE TO RELATED APPLICATIONS

This application is a divisional application of U.S. patent application Ser. No. 12/738,980, filed Jul. 28, 2010, now U.S. Pat. No. 8,440,787, which is a 35 U.S.C. §371 application of International Application No. PCT/US2008/012091, filed Oct. 23, 2008, designating the United States, which claims the benefit of priority under 35 U.S.C. §119(e) to U.S. Provisional Patent Application No. 60/982,012, filed Oct. 23, 2007, both of which are hereby incorporated by reference in their entireties.

FIELD OF THE INVENTION

Among other things, this invention relates to water-soluble, non-peptidic polymers, and conjugates made therefrom, wherein the polymer comprises at least one hydroxyapatite-targeting moiety.

BACKGROUND OF THE INVENTION

Covalent attachment of hydrophilic polymers to molecules having pharmaceutically useful properties is of considerable utility for drug delivery. There is a growing list of polymers whose conjugates have entered clinical trials. Among them are conjugates of polyethylene glycol, abbreviated as "PEG," [Greenwald et al. (2003) Effective drug delivery by PEGylated drug conjugates. *Adv. Drug Delivery Rev.* 55:217-250; Harris et al. (2003) Effect of PEGylation on Pharmaceuticals. *Nat. Rev. Drug Discovery* 2:214-221)], hydroxyethylcellulose, abbreviated as "HES," (WO 2006/050959), poly(L-glutamic acid) [Li (2002) Poly(L-glutamic acid)-anticancer drug conjugates. *Adv. Drug Delivery Rev.* 54: 695-713]. PEG conjugates have been remarkably successful as several are marketed drugs (e.g. CIMZIA®, NEULASTA®, MACUGEN®, SOMAVERT®, PEGASYS®, and PEG-INTRON®). PEG is a polymer that possesses many beneficial properties. For instance, PEG is soluble in water and in many organic solvents, is non-toxic and non-immunogenic, and when attached to a surface, PEG provides a biocompatible, protective coating. Common applications or uses of PEG include (i) covalent attachment to proteins to, for example, extend plasma half-life and reduce clearance through the kidney, (ii) attachment to surfaces such as in arterial replacements, blood contacting devices, and biosensors, (iii) use as a soluble carrier for biopolymer synthesis, and (iv) use as a reagent in the preparation of hydrogels. The other commonly used hydrophilic polymers claim similar properties and potential uses.

In many if not all of the uses noted above, it is necessary to first activate the hydrophilic polymer by converting its active terminus, e.g., a hydroxyl group in the case of a PEG, to a functional group capable of readily reacting with a functional group found within a desired target molecule or surface, such as a functional group found on the surface of a protein. For proteins, typical functional groups include functional groups associated with the side chains of lysine, cysteine, histidine, arginine, aspartic acid, glutamic acid, serine, threonine, and tyrosine, as well as the N-terminal amino functional group and the C-terminal carboxylic acid functional group. Other nontoxic biocompatible hydrophilic polymers may be substituted and are generally acceptable alternatives, with modest changes based on the specific functional groups that are available for use in polymer modification and ultimately conjugation.

Using PEG as representative of the class, PEG used as a starting material for most PEG activation reactions is typically an end-capped PEG. An end-capped PEG is one where one or more of the hydroxyl groups, typically located at a terminus of the polymer, is converted into a non-reactive group, such as a methoxy, ethoxy, or benzyloxy group. Most commonly used is methoxyPEG, abbreviated as mPEG. End-capped PEGs such as mPEG are generally preferred, since such end-capped PEGs are typically more resistant to crosslinking and aggregation. The structures of two commonly employed end-capped PEG alcohols, mPEG and monobenzyl PEG (otherwise known as bPEG), are shown below,

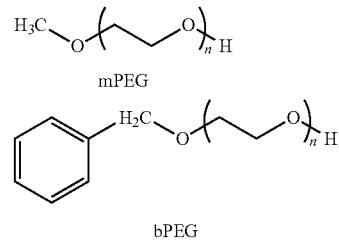

wherein n typically ranges from about 10 to about 2,000.

In one specific example of a polymer reagent for use in drug delivery, U.S. Pat. No. 6,436,386 describes PEG-based, hydroxyapatite-targeting polymers that can be used to selectively target bone surfaces within a patient for delivery of therapeutic agents to the bone site. In this manner, the polymeric reagent provides both targeted delivery of the active portion of the molecule to the tissue of interest and increased circulation time.

Despite many successes, conjugation of a polymer to an active agent is often challenging. For example, it is known that attaching a relatively long poly(ethylene glycol) molecule to an active agent typically imparts greater water solubility than attaching a shorter poly(ethylene glycol) molecule. One of the drawbacks of some conjugates bearing polymer moieties, however, is the possibility that such conjugates may be substantially inactive in vivo. It has been hypothesized that these conjugates are substantially inactive due to the length of the polymer chain, which effectively "wraps" itself around the entire active agent, thereby limiting access to ligands required for pharmacologic activity.

As a result, there is an ongoing need in the art for polymer reagents suitable for conjugation to drug moieties for drug delivery applications, particularly polymer reagents that have the molecular weight necessary to provide a for a conjugate that has the desirable in vivo circulation time, but which also exhibits timely clearance from the body. It would be particularly beneficial for such polymer reagents to also provide the ability to target a particular site of the body, such as hydroxyapatite surfaces. The present invention addresses this and other needs in the art.

SUMMARY OF THE INVENTION

The present invention provides hydroxyapatite-targeting, multiarm polymer reagents suitable for reaction with biologically active agents to form conjugates, the polymeric reagents comprising one or more polymer chains and a plurality of hydroxyapatite-targeting moieties located at the terminus of one or more of the polymer chains. The multiarm polymers are optionally divided or separated by one or more degradable linkages into polymer segments having a molecular weight suitable for renal clearance. The polymeric reagents of the invention can have a substantially linear structure, although branched or multiarm structures are contemplated as well. The invention is suited for applications in which use of a high molecular weight polymer is desired, such as a total polymer number average molecular weight of at least about 30,000 Da for linear polymers and 20,000 Da for multiarm polymers. Each structure includes one or more linkages capable of degradation in vivo. The use of multiple hydroxyapatite-targeting moieties on each polymer molecule enhances the ability of the polymer reagent to selectively target and bind to hydroxyapatite surfaces, which in turn, can increase the concentration of biologically active moiety delivered to the bone site.

In one embodiment, the invention provides a hydroxyapatite-targeting, multiarm polymer having the structure:

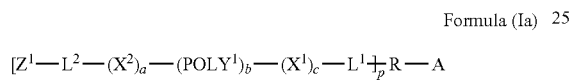

Formula (Ia)

wherein:
A is $-(X^3)_d-(L^3)_e-(X^4)_f$-POLY$^2$-Z$^2$ or $-(X^3)_d-(L^3)_e-(X^4)_f-Z^2$ each POLY$^1$ and POLY$^2$, which may be the same or different, is a water-soluble, non-peptidic polymer;

each X$^1$, X$^2$, X$^3$, and X$^4$, which may be the same or different, is a spacer moiety;

each L$^1$, L$^2$, and L$^3$, which may be the same or different, are linkages;

each Z$^1$, which may be the same or different, is Z$^2$ or a hydroxyapatite-targeting moiety or a multiarm structure comprising 2 to about 10 hydroxyapatite-targeting moieties and optionally including at least one water-soluble, non-peptidic polymer, with the proviso that, when b is zero, at least one Z$^1$ has a multiarm structure comprising one or more polymer arms and with the proviso that at least one Z$^1$ is a hydroxyapatite-targeting moiety;

Z$^2$ is a functional group, optionally attached to POLY$^2$ through a spacer;

each a, b, c, d, e, and f, which may be the same or different, is either zero or one;

R is a monomeric or oligomeric multiarm core molecule derived from a molecule comprising at least p+1 sites available for attachment; and p is an integer in the range of 2-32.

In certain embodiments, each of POLY$^1$ and POLY$^2$ have a number average molecular weight satisfying one or more of the following: less than about 22,000 Da; less than about 15,000 Da; and less than about 8,000 Da. Exemplary polymers for POLY$^1$ and POLY$^2$ include poly(alkylene glycols), poly(olefinic alcohol), poly(vinylpyrrolidone), poly(hydroxyalkylmethacrylamide), poly(hydroxyalkylmethacrylate), poly(saccharides), poly(α-hydroxy acid), poly(acrylic acid), poly(vinyl alcohol), polyphosphazene, polyoxazoline, poly(N-acryloylmorpholine), and copolymers, terpolymers, or mixtures thereof. Examples of the hydroxyapatite-targeting moiety include tetracycline, calcein, bisphosphonates, polyaspartic acid, polyglutamic acid, and aminophosphosugars.

Certain embodiments of the polymer reagents of the invention include at least one hydrolytically or enzymatically cleavable linkage, such as in the linkages at the L$^1$, L$^2$, or L$^3$ position. The polymer chains, such as POLY$^1$ and POLY$^2$, can have a segmented structure comprising two to about five water-soluble, non-peptidic polymer segments attached through linkages. For example, one or both of POLY$^1$ and POLY$^2$ can have a structure according to the formula -POLY-L-POLY-, wherein each POLY is a water-soluble, non-peptidic polymer and L is a linkage, the linkage optionally being degradable.

The terminal Z$^1$ moiety can have a multiarm structure, such as any of the following structures:

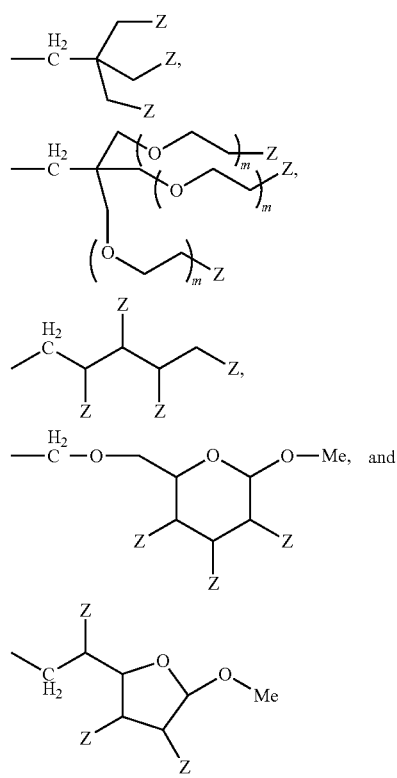

wherein each m is 1-350, Me is methyl, and each Z is a hydroxyapatite-targeting moiety.

The core moiety, R, can be derived from a polyol with the structure R$^1$(OH)$_p$, wherein R is a branched hydrocarbon, optionally including one or more ether linkages, and p is at least 3. Exemplary polyols include glycerol, pentaerythritol, sugar-derived alcohols, and oligomers or polymers thereof. Alternatively, R can be derived from disulfides, peptides, oligomers or polymers thereof, and combinations thereof. In certain embodiments, R is derived from a di-peptide or tri-peptide comprising at least one lysine residue.

Exemplary polymer reagents of the invention include the following polymer structures:

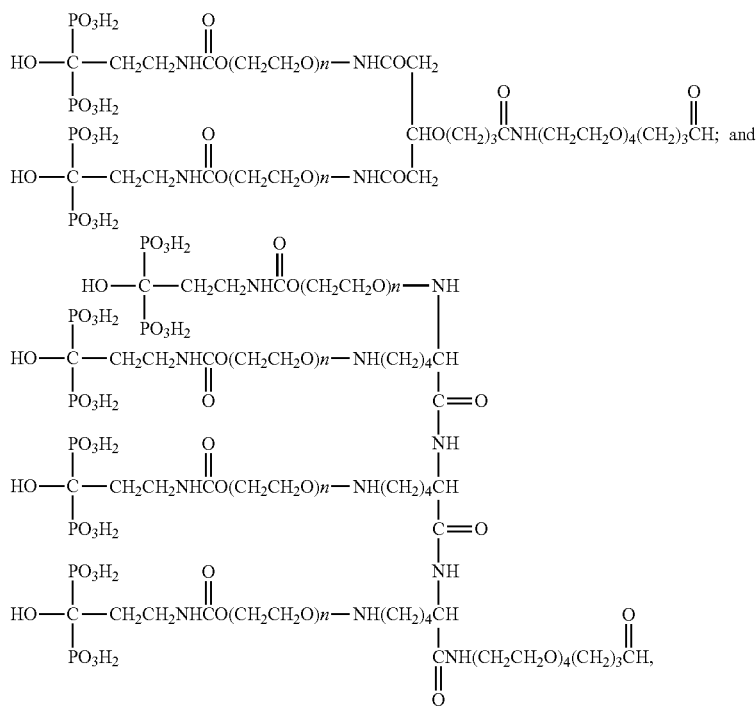

wherein n is 1-350.

In another aspect, the invention provides a hydroxyapatite-targeting, multiarm polymer conjugate comprising the reaction product of the polymer reagent of the invention with a biologically active agent, and having the structure:

Formula (Ib)

wherein all previous variables of Formula (Ia) apply to Formula (Ib) and further wherein B is $-(X^3)_d$-$(L^3)_e$-$(X^4)_f$-POLY$^2$-L$^4$-Drug or $-(X^3)_d$-$(L^3)_e$-$(X^4)_f$-L$^4$-Drug, Drug is a residue of a biologically active moiety, L$^4$ is a linkage resulting from reaction of Z$^2$ with a functional group on the biologically active moiety, and Z$^3$ is L$^5$-Drug or a hydroxyapatite-targeting moiety, wherein L$^5$ is a linkage resulting from reaction of Z$^1$, where Z$^1$ is a functional group, with a functional group on the biologically active moiety, with the proviso that at least one Z$^3$ is a hydroxyapatite-targeting moiety.

The Drug is a residue of a biologically active moiety, which can be, for example, growth factors, antibiotics, chemotherapeutic agents, or analgesics. Exemplary growth factors include fibroblast growth factors, platelet-derived growth factors, bone morphogenic proteins, osteogenic proteins, transforming growth factors, LIM mineralization proteins, osteoid-inducing factors, angiogenins, endothelins; growth differentiation factors, ADMP-1, endothelins, hepatocyte growth factor and keratinocyte growth factor, heparin-binding growth factors, hedgehog proteins, interleukins, colony-stimulating factors, epithelial growth factors, insulin-like growth factors, cytokines, osteopontin, and osteonectin.

Although multiarm structures are most preferred, in another aspect, the invention provides a heterobifunctional, substantially linear, hydroxyapatite-targeting polymer having the structure:

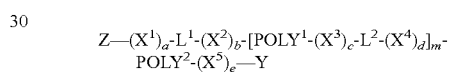

wherein:

each POLY$^1$ and POLY$^2$, which may be the same or different, is a water-soluble, non-peptidic polymer;

each X$^1$, X$^2$, X$^3$, X$^4$, and X$^5$, which may be the same or different, is a spacer moiety;

L$^1$ is a linkage;

each L$^2$ is a hydrolytically or enzymatically cleavable linkage selected from the group consisting of carbamate and amide;

Z is a hydroxyapatite-targeting moiety;

Y is a functional group;

each a, b, c, d, and e, which may be the same or different, is either zero or one; and m is an integer in the range of 1-10.

In addition to polymer reagents and conjugates made therefrom, the invention includes methods of making such reagents and conjugates, as well as therapeutic methods of using biologically active conjugates of polymer reagents of the invention.

DETAILED DESCRIPTION OF THE INVENTION

Before describing the present invention in detail, it is to be understood that this invention is not limited to the particular polymers, synthetic techniques, active agents, and the like as such may vary. It is also to be understood that the terminology used herein is for describing particular embodiments only, and is not intended to be limiting.

It must be noted that, as used in this specification, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

I. Definitions

In describing and claiming the present invention, the following terminology will be used in accordance with the definitions described below.

"PEG," "polyethylene glycol" and "poly(ethylene glycol)" are used herein to mean any water-soluble poly(ethylene oxide). Typically, PEGs for use in the present invention will comprise one of the two following structures: "—O(CH$_2$CH$_2$O)$_n$—" or "—CH$_2$CH$_2$O(CH$_2$CH$_2$O)$_n$—CH$_2$CH$_2$—," where n is 3 to 3000, and the terminal groups and architecture of the overall PEG may vary. "PEG" means a polymer that contains a majority, that is to say, greater than 50%, of subunits that are —CH$_2$CH$_2$O—.

One commonly employed PEG is end-capped PEG. When PEG is defined as "—O(CH$_2$CH$_2$O)$_n$—," the end-capping group is generally a carbon-containing group typically comprised of 1-20 carbons and is preferably alkyl (e.g., methyl, ethyl or propyl) although saturated and unsaturated forms thereof, as well as aryl, heteroaryl, cyclo, heterocyclo, and substituted forms of any of the foregoing are also envisioned. When PEG is defined as "—CH$_2$CH$_2$O(CH$_2$CH$_2$O)$_n$—CH$_2$CH$_2$—," the end-capping group is generally a carbon-containing group typically comprised of 1-20 carbon atoms and an oxygen atom that is covalently bonded to the group and is available for covalently bonding to one terminus of the PEG. In this case, the group is typically, alkoxy (e.g., methoxy, ethoxy or benzyloxy) and with respect to the carbon-containing group can optionally be saturated and unsaturated, as well as aryl, heteroaryl, cyclo, heterocyclo, and substituted forms of any of the foregoing. The other ("non-end-capped") terminus is a typically hydroxyl, amine or an activated group that can be subjected to further chemical modification when PEG is defined as "—CH$_2$CH$_2$O(CH$_2$CH$_2$O)$_n$—CH$_2$CH$_2$—." In addition, the end-capping group can also be a silane.

Specific PEG forms for use in the invention include PEGs having a variety of molecular weights, structures or geometries (e.g., branched, linear, multiarm, and the like), to be described in greater detail below.

The end-capping group can also advantageously comprise a detectable label. When the polymer has an end-capping group comprising a detectable label, the amount or location of the polymer and/or the moiety (e.g., active agent) of interest to which the polymer is coupled can be determined by using a suitable detector. Such labels include, without limitation, fluorescers, chemiluminescers, moieties used in enzyme labeling, colorimetric (e.g., dyes), metal ions, radioactive moieties, and the like.

The polymers used in the methods described herein are typically polydisperse (i.e., number average molecular weight and weight average molecular weight of the polymers are not equal). The polymers prepared in accordance with the methods described herein, however, possess low polydispersity values—expressed as a ratio of weight average molecular weight (Mw) to number average molecular weight (Mn), (Mw/Mn)—generally less than about 1.3, preferably less than about 1.2, more preferably less than about 1.15, still more preferably less than about 1.05, yet still most preferably less than about 1.04, and most preferably less than about 1.03. It is noted that the polydispersity of a multiarm PEG could be much higher than the polydispersity of the polymer arms used to create the multiarm PEG.

As used herein, the term "ionizable functional group" and variations thereof is a functional group that may gain or lose a proton by interaction with another ionizable species of functional group in aqueous or other polar media. Ionizable functional groups include, but are not limited to, amine, carboxylic acids, aldehyde hydrates, ketone hydrates, amides, hydrazines, thiols, phenols, oximes, dithiopyridines, and vinylpyridines.

As used herein, the term "carboxylic acid" is a moiety having a

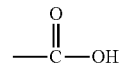

functional group [also represented as a "—COOH" or —C(O)OH], as well as moieties that are derivatives of a carboxylic acid, such derivatives including, for example, protected carboxylic acids. Thus, unless the context clearly dictates otherwise, the term carboxylic acid includes not only the acid form, but corresponding esters and protected forms as well. Reference is made to Greene et al., "PROTECTIVE GROUPS IN ORGANIC SYNTHESIS" 3$^{rd}$ Edition, John Wiley and Sons, Inc., New York, 1999.

"Activated carboxylic acid" means a functional derivative of a carboxylic acid that is more reactive than the parent carboxylic acid, in particular, with respect to nucleophilic acyl substitution. Activated carboxylic acids include but are not limited to acid halides (such as acid chlorides), anhydrides, amides and esters.

The term "reactive" or "activated", when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "nonreactive" or "inert" group).

The terms "protected" or "protecting group" or "protective group" refer to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene et al., supra.

As used herein, the term "functional group" or any synonym thereof is meant to encompass protected forms thereof.

The term "spacer" or "spacer moiety" is used herein to refer to an atom or a collection of atoms optionally used to link interconnecting moieties such as a terminus of a water-soluble polymer and a functional group. The spacer moieties of the invention may be hydrolytically stable or may include a physiologically hydrolyzable or enzymatically degradable linkage.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include ethyl, propyl, butyl, pentyl, 2-methylbutyl, 2-ethylpropyl, and the like. As used herein, "alkyl" includes cycloalkyl when alkyl can include three or more carbon atoms.

"Lower alkyl" refers to an alkyl group containing from 1 to 6 carbon atoms, and may be straight chain or branched, as exemplified by methyl, ethyl, n-butyl, iso-butyl, tert-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl (e.g., 0-2 substituted phenyl); substituted phenyl; and the like.

"Substituted aryl" is aryl having one or more non-interfering groups as a substituent. For substitutions on a phenyl ring, the substituents may be in any orientation (i.e., ortho, meta, or para).

"Alkoxy" refers to an —O—R group, wherein R is alkyl or substituted alkyl, preferably $C_1$-$C_{20}$ alkyl (e.g., methoxy, ethoxy, propyloxy, benzyloxy, etc.), more preferably $C_1$-$C_8$ alkyl.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Electrophile" refers to an ion or atom or collection of atoms, that may be ionic, having an electrophilic center, i.e., a center that is electron seeking or capable of reacting with a nucleophile.

"Nucleophile" refers to an ion or atom or collection of atoms, that may be ionic, having a nucleophilic center, i.e., a center that is seeking an electrophilic center or capable of reacting with an electrophile.

A linkage that is "cleavable in vivo" refers to linkages capable of being cleaved while in circulation in vivo by a hydrolytic process, an enzymatic process, a chemical process, or a combination of such processes. In other words, linkages that are cleavable in vivo are those linkages that can break apart under physiological conditions (i.e., at about pH 7 to 7.5 and temperature of about 37° C. in the presence of serum or other body fluids). The degradation half-life of the linkage can vary, but is typically in the range of about 0.1 to about 10 days under physiologic conditions.

A "hydrolytically cleavable" or "hydrolyzable" or "hydrolytically degradable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to, carboxylate ester, phosphate ester, anhydrides, acetals, ketals, acyloxyalkyl ether, imines, orthoesters, and oligonucleotides.

An "enzymatically degradable linkage" means a linkage that is subject to degradation by one or more enzymes under physiological conditions. The enzymatic degradation process may also include a hydrolysis reaction. Enzymatically degradable linkages can include certain amide (—C(O)—NH—) and urethane (—O—C(O)—NH—) linkages, especially when in a proximate arrangement with other groups of atoms that may provide either activation for degradation or additional sites needed for attraction of an enzyme. For example, a urethane in proximate location with certain amides, e.g. —O—C(O)—NH—CHY—C(O)—NH—Y', where Y is H, alkyl, substituted alkyl (e.g., arylalkyl, hydroxylalkyl, thioalkyl, etc.), or aryl, and Y' is alkyl or substituted alkyl, are enzymatically degradable. As defined herein, "urethane" linkages are inclusive of linkages having the above structure.

A "chemically degradable" linkage as used herein is a linkage that degrades through chemical reaction under physiologic conditions in vivo. For example, disulfide (—S—S—) bonds can be degraded in vivo through chemical reaction with glutathione.

A "hydrolytically stable" or "non-degradable" linkage or bond refers to a chemical bond, typically a covalent bond, that is substantially stable in water, meaning it does not undergo hydrolytic or enzymatic cleavage under physiological conditions to any appreciable extent over an extended period of time. Examples of hydrolytically stable linkages include but are not limited to the following: carbon-carbon bonds (e.g., in aliphatic chains), ethers, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Multifunctional" or "multisubstituted" in the context of a polymer or polyol means a polymer or polyol having two or more functional groups contained therein, where the functional groups may be the same or different. Multifunctional polymers or polyols of the invention will typically contain a number of functional groups satisfying one or more of the following ranges: from about 2-100 functional groups, from 2-50 functional groups, from 2-25 functional groups, from 2-15 functional groups, from 2 to 10 functional groups. Thus, the number of functional groups in the polymer backbone or polyol can be any one of 2, 3, 4, 5, 6, 7, 8, 9 or 10 functional groups.

A "difunctional" or "disubstituted" polymer or polyol means a polymer or polyol having two functional groups contained therein, either the same (i.e., homodifunctional) or different (i.e., heterodifunctional).

A "monofunctional" or "monosubstituted" polymer means a polymer having a single functional group contained therein (e.g., an mPEG based polymer).

A basic or acidic reactant described herein includes neutral, charged, and any corresponding salt foams thereof.

The twin "patient," refers to a living organism suffering from or prone to a condition that can be prevented or treated by administration of a conjugate, and includes both humans and animals.

"Optional" or "optionally" means that the subsequently described circumstance may or may not occur, so that the description includes instances where the circumstance occurs and instances where it does not.

Unless otherwise noted, molecular weight is expressed herein as number average molecular weight ($M_n$), which is defined as $$\frac{\sum N_i M_i}{\sum N_i},$$

wherein Ni is the number of polymer molecules (or the number of moles of those molecules) having molecular weight Mi.

Each of the terms "drug," "biologically active molecule," "biologically active moiety," "active agent" and "biologically active agent", when used herein, means any substance which can affect any physical or biochemical property of a biological organism, including but not limited to viruses, bacteria, fungi, plants, animals, and humans. In particular, as used herein, biologically active molecules include any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, polynucleotides, nucleic acids, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

As used herein, "non-peptidic" refers to a polymer backbone substantially free of peptide linkages. However, the polymer backbone may include a minor number of peptide linkages spaced along the length of the backbone, such as, for example, no more than about 1 peptide linkage per about 50 monomer units.

The term "conjugate" is intended to refer to the entity formed as a result of covalent attachment of a molecule, e.g., a biologically active molecule, to a reactive polymer molecule, preferably a polyethylene glycol) bearing one or more reactive groups.

II. Hydroxyapatite-Targeting Polymers and Conjugates Made Therefrom

In one aspect, the present invention provides polymeric reagents, and conjugates with biologically active agents made using the polymeric reagents, characterized by the presence of a plurality of hydroxyapatite-targeting moieties. The use of a plurality of hydroxyapatite-targeting moiety in a single polymer structure can enhance binding of the polymer to a bone surface, which could potentially increase the residence time of a drug molecule attached to the polymer structure at the bone site.

A generalized structure of a multiarm polymer of the invention is shown below, which includes bone-targeting moieties and a reactive handle that can be used to conjugate a therapeutic agent. The number of bone-targeting moieties (BTM) may vary extensively from two to more than twenty, depending on the binding efficiency of the particular BTM. The polymer molecular weight can be adjusted as desired to provide maximum efficiency in the various roles that the polymer plays, e.g., circulation time, solubility, protection of the drug, and carrier of the BTMs.

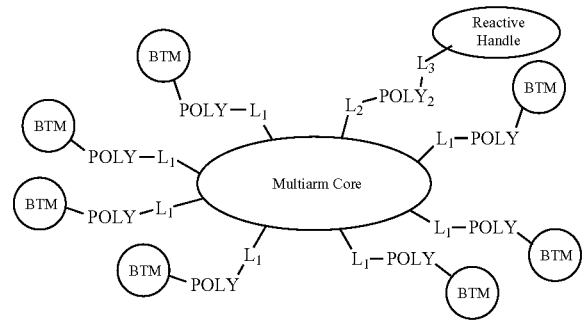

BTM = Bone-targeting Moiety wherein each POLY and the optional $POLY_2$ is a water-soluble, non-peptidic polymer, BTM is a bone-targeting moiety (used herein interchangeably with hydroxyapatite-targeting moiety), and $L_1$, $L_2$, and $L_3$ are linkages. Conjugation of the "reactive handle" with a therapeutic agent, such as a drug that may target bone cancer cells, makes the polymer-bound drug a targeting drug for bone cells. In application, the drug could be injected directly into the cancerous portion of the bone for action.

The reactive handle is preferably an ionizable functional group that can be utilized in manipulation and purification of the molecule. Exemplary ionizable functional groups include amine and carboxylic acid groups such as alkanoic acids having a carbon length (including the carbonyl carbon) of 1 to about 25 carbon atoms (e.g., carboxymethyl, propanoic acid, and butanoic acid). Examples of other suitable functional groups include aldehyde hydrate, ketone hydrate, amide, hydrazine, hydrazide, thiol, sulfonic acid, amidate, hydroxylamine, phenol, oxime, dithiopyridine, vinylpyridine, 2-substituted-1,3-oxazoline, 2-substituted 1,3-(4H)-dihydrooxazines, 2-substituted-1,3-thiazoline, and 2-substituted 1,3-(4H)-dihydrothiazines.

An alternate generalized structure of a multiarm polymer of the invention is shown below, which includes a single bone-targeting moiety and several sites containing therapeutic agents. Again, the number BTMs may vary extensively from one to several, depending on the binding efficiency of the particular BTM, but the preferred number of BTM units is low. The polymer molecular weight can be adjusted as desired to provide maximum efficiency in the various roles that the polymer plays, e.g., circulation time, solubility, and carrier of the BTMs. The drug moieties in this application would be low molecular weight units that alternatively could be attached to the polymer by a degradable linkage that would allow delivery of the drug at the targeted site.

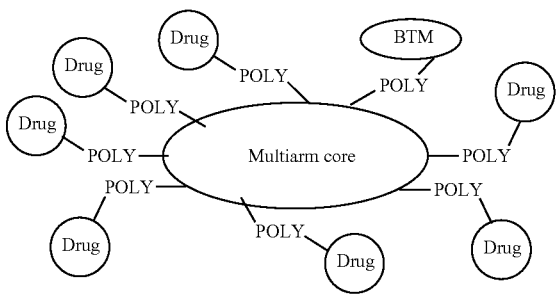

The polymer reagents may also include one or more cleavable or degradable linkages that degrade in vivo. The degradable linkage or linkages are spaced along the polymer chain or within a central core molecule such that each segment of polymeric reagent that is released upon degradation of the linkage in vivo has a molecular weight that does not impede renal clearance of the segment. The polymeric reagents of the present invention are particularly advantageous in that they can be used to prepare conjugates where both a relatively high polymer molecular weight is desired along with substantially complete elimination of the polymer from the body. For example, the total polymer number average molecular weight for the polymeric reagent (and the conjugate prepared therefrom) is typically at least about 30,000 Da, such as a molecular weight of about 30,000 to about 150,000 Da (e.g., total molecular weights of about 30,000 Da, 35,000 Da, 40,000 Da, 45,000 Da, 50,000 Da, 55,000 Da, 60,000 Da, 65,000 Da, 70,000 Da, and the like). The number average molecular weight of each polymer segment released upon degradation of the degradable linkages is preferably less than or equal to about 22,000 Da, more preferably less than or equal to about 20,000 Da, even more preferably less than or equal to about 15,000 Da, and most preferably less than or equal to about 8,000 Da. In some embodiments, the polymer segments have a molecular weight of no more than about 5,000 Da, or no more than about 2,500 Da. The number of polymer segments resulting from cleavage of the degradable linkages can vary from 2 to about 40, but is generally in the range of 2 to about 10 (e.g., 2, 3, 4, 5, 6, 7, 8, 9, or 10 polymer segments).

The structural configuration of the polymeric reagents (and the conjugates prepared therefrom) of the invention can vary. Although less preferred, the polymeric reagents can have a substantially linear form. Preferred embodiments of the polymeric reagent have a "multiarm" configuration comprising two or more (preferably three or more) polymer arms extending from a common multifunctional core molecule, such as a polyol or peptide. Preferred embodiments of the polymers of the invention are not in the form of a hydrogel, meaning the polymeric reagents (and the conjugates prepared therefrom) are not crosslinked to a substantial degree with other polymers in a water-swellable matrix.

The degradable linkages within the polymeric reagents (and the conjugates prepared therefrom) can vary. It is preferable to use degradable linkages cleavable in vivo, and having a half-life of between about 0.1 and about 10 days under physiological conditions (i.e., at a pH of 7-7.5 and a temperature of about 37° C.). The rate of degradation of a linkage can be measured by analytical determination of liberated polymer segments using gel permeation chromatography ("GPC"). Although the polymeric reagents of the invention can include one or more carbonate groups as a degradable linkage, it is preferable for the polymeric reagents to comprise at least one degradable linkage that does not include a carbonate group, and polymeric reagents without any carbonate groups are contemplated.

Exemplary degradable linkages include, but are not limited to, ester linkages; carbonate linkages; carbamates; imides; disulfides; di-, tri-, or tetrapeptides; imine linkages resulting, for example, from reaction of an amine and an aldehyde (see, e.g., Ouchi et al. (1997) *Polymer Preprints* 38(1):582-3, which is incorporated herein by reference); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; ortho ester linkages that are, for example, formed by reaction between a formate and an alcohol; and oligonucleotide linkages formed by, for example, a phosphoramidite group, e.g., at the end of a polymer, and a 5' hydroxyl group of an oligonucleotide.

Amide and urethane bonds are generally considered stable groups for binding PEGs to proteins such as interferon, e.g., K. R. Reddy, M. W. Modi and S. Pedder (2002) *Adv. Drug Delivery Rev.* 54:571-586. Some cleavage of these stable groups, however, may occur in vivo. For example, in a PEG interferon (marketed under the "PEGASYS®" brand), up to 30% of the PEG associated with the conjugate is cleared by cleavage of a urethane bond (see M. W. Modi, J. S. Fulton, D. K. Buckmann, T. L. Wright, D. J. Moore (2000) "Clearance of Pegylated (40 kDa) interferon alpha-2a (PEGASYS®) is Primarily Hepatic, *Hepatology* 32: 371A). The mechanism for the overall clearance of the conjugate is fairly slow and takes several days.

With respect to amide bounds, there are special cases where amide bonds, such as those found in peptide linkages, are susceptible to enzymatic cleavage. Suzawa et al. (2000) *Bioorg. Med. Chem.* 8(8):2175-84) found that a poly(ethylene glycol) bound L-alanine-valine di-peptide linkage cleaved in the presence of the model enzyme thermolysin. Additional examples of peptide linkages (e.g., di-peptide or tri-peptide linkages) that may find use in the present invention can be found in U.S. Pat. Nos. 5,286,637 and 6,103,236; Goff and Carroll (1990) *Bioconjugate Chem.* 1:381-386); and Huang et al. (1998) *Bioconjugate Chem.* 9:612-617). Thus, in certain embodiments, the degradable linkage(s) contained within the polymeric reagents (and the conjugates formed therefrom) can include amide or urethane linkages.

Esters, though more susceptible than amides and urethanes to hydrolytic cleavage, are also readily cleaved by enzymatic processes, thus making esters especially labile linkages in vivo. Esters are more resistant to enzymatic cleavage if they have groups in the vicinity of the functional group that sterically block the approach of an enzyme. Hence, including this type of sterically hindered ester function may cause an ester group to be an attractive linker for applications where it is desirable for the polymer to break down hydrolytically or enzymatically in a few hours to a few days.

The groups that best facilitate stability through steric hindrance are groups (e.g., alkyl groups) located at the position alpha to the carbonyl carbon of the ester, as is the case with the two ester-containing polymers below (wherein "POLY" is a water-soluble, non-peptidic polymer). In selecting a structure to present a steric hindrance to enzymatic cleavage, it is preferred to not include a group that has an electron withdrawing effect on the carbonyl group. While not wishing to be bound by theory, such electron withdrawing groups would tend to accelerate acid- or base-catalyzed hydrolysis.

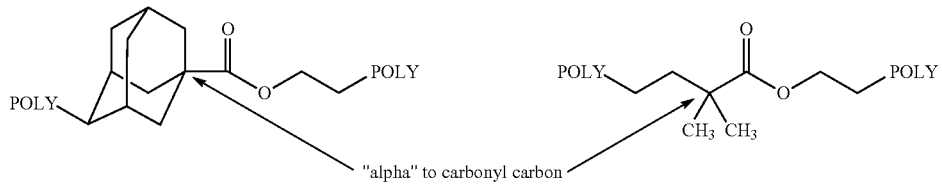

Steric hindrance in the alkyl portion (e.g., the portion or atoms proximal to the oxygen atom, which, in turn, is attached to the carbonyl carbon) of the ester may also slow enzymatic cleavage of esters. Thus, when steric hindrance is desired to influence the rate of enzymatic cleavage, it is contemplated to add steric hindrance at the alpha and/or beta positions relative to the carbonyl carbon and/or the oxygen atom, which, in turn, is attached to the carbonyl carbon of the ester group. It is important, however, to add a combination of steric crowding and electron donation so as to facilitate electrophilic cleavage of the ester by a $S_N1$ pathway. Further, it is important to not make the alkyl portion such a good leaving group, by substitution of electron withdrawing groups, that base catalyzed hydrolysis is favorable. A balance can be achieved by the introduction of mild steric retardation at the alpha and beta positions of the oxygen atom, which, in turn, is attached to the carbonyl carbon of the ester group, as shown in the structure below.

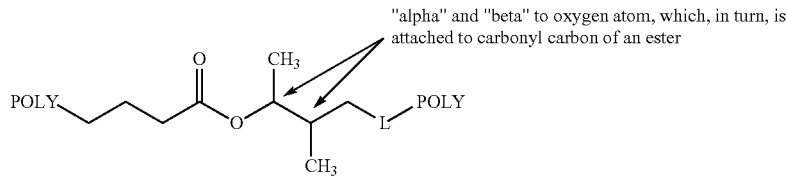

wherein L is a spacer moiety or a linkage resulting from reaction of POLY with an ester-containing moiety and POLY is a water-soluble, non-peptidic polymer.

Thus, preferred steric hindering groups include alkyl groups (e.g., C1-C10 alkyl groups) or aryl groups (e.g., C6-C10 aryl groups) positioned adjacent to the carbonyl carbon and/or adjacent to the oxygen atom attached to the carbonyl group of the ester (i.e., at the alpha or beta positions), and most preferably adjacent to the carbonyl carbon.

It is possible to determine whether any given proposed group is suited for providing the desired steric hindrance by preparing the polymeric reagent with the proposed group. Following formation of the conjugate from the proposed polymeric reagent, the conjugate is subsequently administered the conjugate to a patient or added to a suitable model. Following administration to the patient (or addition to the suitable model), the degradative rate for each degradable linkage within the conjugate can be determined by, for example, taking a blood sample (or aliquot of liquid from the suitable model) and identifying degradative components of the conjugate through chromatographic techniques. The proposed group is suited for providing the desired steric hindrance if the overall degradation rate falls within a desired range and/or is improved over a control polymeric reagent tested under the same conditions.

The water-soluble, non-peptidic polymers (e.g., $POLY^1$, $POLY^2$, and so forth) that make up part of the polymeric reagents of the present invention should be non-toxic and biocompatible, meaning that the polymer is capable of coexistence with living tissues or organisms without causing harm. It is to be understood that the polymer can be any of a number of water-soluble, non-peptidic polymers. Preferably, poly(ethylene glycol) (i.e., PEG) is the polymer used to form the polymeric reagents described herein. Examples of other suitable polymers include, but are not limited to, other poly(alkylene glycols), copolymers of ethylene glycol and propylene glycol, poly(olefinic alcohol), poly(vinyipyrroiidone), poly(hydroxyalkylmethacrylamide), poly(hydroxyalkylmethacrylate), poly(saccharides), poly(α-hydroxy acid), poly(acrylic acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Different polymers can be incorporated into the same polymer backbone. Any combination of water soluble and non-peptidic polymers is encompassed within the present invention. Each polymer segment (e.g., each $POLY^1$ or $POLY^2$) can also comprise two or more polymer segments connected by cleavable or stable linkages.

The polymers can be in substantially linear form or a multiarm or branched form, such as the branched PEG molecules set forth in U.S. Pat. No. 5,932,462, which is incorporated by reference herein in its entirety. Generally speaking, a multi-armed or branched polymer possesses two or more polymer "arms" extending from a central branch point. For example, an exemplary branched PEG polymer has the structure:

Formula IV wherein $PEG_1$ and $PEG_2$ are PEG polymers in any of the forms or geometries described herein, and which can be the same or different, and L' is a hydrolytically stable linkage. An exemplary branched PEG of Formula I has the structure:

Formula IVa wherein: $poly_a$ and $poly_b$ are PEG backbones, such as hydroxy poly(ethylene glycol); R" is a nonreactive moiety, such as H, methyl or a PEG backbone; and P and Q are nonreactive linkages. In a preferred embodiment, the branched PEG polymer is hydroxy poly(ethylene glycol) disubstituted lysine.

The branched PEG structure of Formula IV can be attached to a third oligomer or polymer chain as shown below:

Formula V wherein $PEG_S$ is a third PEG oligomer or polymer chain, which can be the same or different from $PEG_1$ and $PEG_2$.

In another embodiment, the branched PEG used in the invention has the structure:

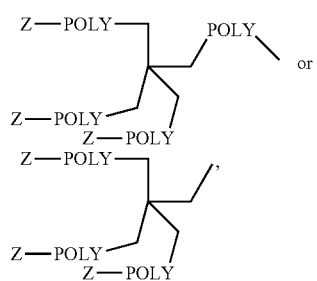

wherein each POLY is a water-soluble, non-peptidic polymeric or oligomeric segment (e.g., a PEG segment), and each Z is a capping group, a functional group, or a bone-targeting group.

As evidenced in the exemplary polymeric structures below, the polymeric reagents of the invention will typically include one or more functional groups suitable for reaction with a complementary functional group on a biologically active agent in order to form a covalent linkage (which can optionally be cleavable in vivo) between the polymeric reagent and the active agent. Examples of suitable functional groups include hydroxyl, active ester (e.g., N-hydroxysuccinimidyl ester and 1-benzotriazolyl ester), active carbonate (e.g., N-hydroxysuccinimidyl carbonate, 1-benzotriazolyl carbonate, and p-nitrophenyl carbonate), acetal, aldehyde having a carbon length of 1 to 25 carbons (e.g., acetaldehyde, propionaldehyde, and butyraldehyde), aldehyde hydrate, alkenyl, acrylate, methacrylate, acrylamide, active sulfone, amine, hydrazide, thiol, alkanoic acids having a carbon length (including the carbonyl carbon) of 1 to about 25 carbon atoms (e.g., carboxylic acid, carboxymethyl, propanoic acid, and butanoic acid), acid halide, isocyanate, isothiocyanate, maleimide, vinylsulfone, dithiopyridine, vinylpyridine, iodoacetamide, epoxide, glyoxal, dione, mesylate, tosylate, and tresylate. Exemplary functional groups are discussed in the following references: N-succinimidyl carbonate (see e. U.S. Pat. Nos. 5,281,698, 5,468,478), amine (see, e.g., Buckmann et al. Makromol. Chem. 182:1379 (1981), Zalipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al., Makromol. Chem. 180:1381 (1979), succinimidyl ester (see, e.g., U.S. Pat. No. 4,670, 417), benzotriazole carbonate (see, e.g., U.S. Pat. No. 5,650, 234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11:141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824,784, U.S. Pat. No. 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900,461). All of the above references are incorporated herein by reference.

In certain embodiments, the capping group, functional group, or hydroxyapatite-targeting group (a "Z" moiety such as $Z^1$, $Z^2$, $Z^3$, and so forth) of the polymeric reagents (and the conjugates formed therefrom) will have a multiarm structure. For example, the "Z" moiety can be a multiarm reactive structure comprising 2 to about 10 functional groups (e.g., 2, 3, 4, 5, 6, 7, 8, 9, or 10 functional groups). Exemplary multiarm groups include those having the structure

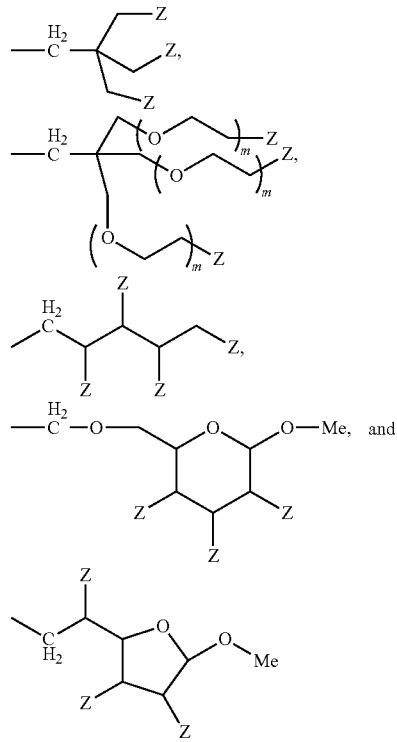

wherein each Z, which may be the same or different, is a functional group, a capping group, or a hydroxyapatite targeting group, optionally including a spacer moiety, and m is an integer in the range of 1 to about 350, preferably 1 to about 10, more preferably 1 to about 4.

The polymeric reagents (and the conjugates formed therefrom) may include one or more spacer moieties (an "X" moiety such as $X^1$, $X^2$, $X^3$, $X^4$, $X^5$, $X^6$, $X^7$, $X^8$, $X^9$, and so forth), particularly located on either side of degradable or stable linkages resulting from reaction of two polymer species or a polymer and a biologically active agent. Exemplary spacer moieties include —C(O)O—, —OC(O)—, —CH$_2$—C(O)O—, —CH$_2$—OC(O)—, —C(O)O—CH$_2$—, —OC(O)—CH$_2$—, —C(O)—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—CH$_2$—, —CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—

—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_h$—(OCH$_2$CH$_2$)$_j$—, —NH—C(O)—O—[CH$_2$]$_h$—(OCH$_2$CH$_2$)$_j$—, bivalent cycloalkyl group, —O—, —S—, an amino acid, a di- or tri-peptide, —N(R$^6$)—, and combinations of two or more of any of the foregoing, wherein R$^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20. Other specific spacer moieties have the following structures: —C(O)—NH—(CH$_2$)$_{1-6}$—NH—C(O)—, —NH—C(O)—NH—(CH$_2$)$_{1-6}$—NH—C(O)—, and —O—C(O)—NH—(CH$_2$)$_{1-6}$—NH—C(O)—, wherein the subscript values following each methylene indicate the number of methylenes contained in the structure, e.g., (CH$_2$)$_{1-6}$ means that the structure can contain 1, 2, 3, 4, 5 or 6 methylenes. The spacer moiety may also comprise an ethylene oxide oligomer/polymer chain comprising 1 to 25 ethylene oxide monomer units [i.e., —(CH$_2$CH$_2$O)$_{1-25}$], either in addition to the above-described spacer moieties or in lieu thereof. When used in addition to another spacer moiety, the ethylene oxide oligomer chain can occur before or after the spacer moiety, and optionally in between any two atoms of a spacer moiety comprised of two or more atoms.

Preferred biologically active agents for use in the conjugates of the invention include active agents having relatively low water solubility, such as certain proteins, peptides, and small molecule drugs. Particularly preferred biologically active agents include those that are intended to have a biological effect on bone tissue within the patient, such as growth factors, antibiotics, chemotherapeutic agents, or analgesics. Exemplary growth factors include fibroblast growth factors, platelet-derived growth factors, bone morphogenic proteins, osteogenic proteins, transforming growth factors, LIM mineralization proteins, osteoid-inducing factors, angiogenins, endothelins; growth differentiation factors, ADMP-1, endothelins, hepatocyte growth factor and keratinocyte growth factor, heparin-binding growth factors, hedgehog proteins, interleukins, colony-stimulating factors, epithelial growth factors, insulin-like growth factors, cytokines, osteopontin, and osteonectin.

Other examples of relatively hydrophobic active agents that can be covalently attached to polymeric reagents of the invention include, but are not limited to, abietic acid, aceglatone, acenaphthene, acenocoumarol, acetohexamide, acetomeroctol, acetoxolone, acetyldigitoxins, acetylene dibromide, acetylene dichloride, acetylsalicylic acid, alantolactone, aldrin, alexitol sodium, allethrin, allylestrenol, alprazolam, aluminum bis(acetylsalicylate), ambucetamide, aminochlothenoxazin, aminoglutethimide, amyl chloride, androstenediol, anethole trithone, anilazine, anthralin, Antimycin A, aplasmomycin, arsenoacetic acid, asiaticoside, astemizole, aurodox, aurothioglycanide, 8-azaguanine, azobenzene, baicalein, Balsam Peru, Balsam Tolu, barban, baxtrobin, bendazac, bendazol, bendroflumethiazide, benomyl, benzathine, benzestrol, benzodepa, benzoxiquinone, benzphetamine, benzthiazide, benzyl benzoate, benzyl cinnamate, bibrocathol, bifenox, binapacryl, bioresmethrin, bisabolol, bisacodyl, bis(chlorophenoxy)methane, bismuth iodosubgallate, bismuth subgallate, bismuth tannate, Bisphenol A, bithionol, bornyl, bromoisovalerate, bornyl chloride, bornyl isovalerate, bornyl salicylate, brodifacoum, bromethalin, broxyquinoline, bufexamac, butamirate, butethal, buthiobate, butylated hydroxyanisole, butylated hydroxytoluene, calcium iodostearate, calcium saccharate, calcium stearate, capobenic acid, captan, carbamazepine, carbocloral, carbophenotin, carboquone, carotene, carvacrol, cephaeline, cephalin, chaulmoogric acid, chenodiol, chitin, chlordane, chlorfenac, chlorfenethol, chlorothalonil, chlorotrianisene, chlorprothixene, chlorquinaldol, chromonar, cilostazol, cinchonidine, citral, clinofibrate, clofaziminc, clofibrate, cloflucarban, clonitrate, clopidol, clorindione, cloxazolam, coroxon, corticosterone, cournachlor, coumaphos, coumithoate cresyl acetate, crimidine, crufomate, cuprobam, cyamemazine, cyclandelate, cyclarbamate cymarin, cyclosporin A, cypermethril, dapsone, defosfamide, deltamethrin, deoxycorticosterone acetate, desoximetasone, dextromoramide, diacetazoto, dialifor, diathymosulfone, decapthon, dichlofluani, dichlorophen, dichlorphenamide, dicofol, dicryl, dicumarol, dienestrol, diethylstilbestrol, difenamizole, dihydrocodeinone enol acetate, dihydroergotamine, dihydromorphine, dihydrotachysterol, dimestrol, dimethisterone, dioxathion, diphenane, N-(1,2-diphenylethyl)nicotinamide, 3,4-di-[1-methyl 6-nitro-3-indolyl]-1H-pyrrole-2,5-dione (MNIPD), dipyrocetyl, disulfamide, dithianone, doxenitoin, drazoxolon, durapatite, edifenphos, emodin, enfenamic acid, erbon, ergocorninine, erythrityl tetranitrate, erythromycin stearate, estriol, ethaverine, ethisterone, ethyl biscournacetate, ethylhydrocupreine, ethyl menthane carboxamide, eugenol, euprocin, exalamide, febarbamate, fenalamide, fenbendazole, fenipentol, fenitrothion, fenofibrate, fenquizone, fenthion, feprazone, flilpin, filixic acid, floctafenine, fluanisone, flumequine, fluocortin butyl, fluoxymesterone, fluorothyl, flutazolam, fumagillin, 5-furftiryl-5-isopropylbarbituric acid, fusaftmgine; glafenine, glucagon, glutethimide, glybuthiazole, griseofulvin, guaiacol carbonate, guaiacol phosphate; halcinonide, hematoporphyrin, hexachlorophene, hexestrol, hexetidine, hexobarbital, hydrochlorothiazide, hydrocodone, ibuproxam, idebenone, indomethacin, inositol niacinate, iobenzamic acid, iocetamic acid, iodipamide, iomeglamic acid, ipodate, isometheptene, isonoxin, 2-isovalerylindane-1,3-dione, josamycin, 11-ketoprogesterone, laurocapram, 3-O-lauroylpyridoxol diacetate, lidocaine, lindane, linolenic acid, liothyronine, lucensomycin, mancozeb, mandelic acid, isoamyl ester, mazindol, mebendazole, mebhydroline, mebiquine, melarsoprol, melphalan, menadione, menthyl valerate, mephenoxalone, mephentermine, mephenyloin, meprylcaine, mestanolone, mestranol, mesulfen, metergoline, methallatal, methandriol, methaqualone, methylcholanthrene, methylphenidate, 17-methyltestosterone, metipranolol, minaprine, myoral, naftalofos, naftopidil, naphthalene, 2-naphthyl lactate, 2-(2-naphthyloxy)ethanol, naphthyl salicylate, naproxen, nealbarbital, nemadectin, niclosamide, nicoclonate, nicomorphine, nifuroquine, nifuroxazide, nitracrine, nitromersol, nogalamycin, nordazepam, norethandrolone, norgestrienone, octaverine, oleandrin, oleic acid, oxazepam, oxazolam, oxeladin, oxwthazaine, oxycodone, oxymesterone, oxyphenistan acetate, paclitaxel, paraherquamide, parathion, pemoline, pentaerythritol tetranitrate, pentylphenol, perphenazine, phencarbamide, pheniramine, 2-phenyl-6-chlorophenol, phenthnethyl-barbituric acid, phenyloin, phosalone, O-phthalylsulfathiazole, phylloquinone, picadex, pifamine, piketopfen, piprozolin, pirozadil, pivaloyloxymethyl butyrate, plafibride, plaunotol, polaprezinc, polythiazide, probenecid, progesterone, promegestone, propanidid, propargite, propham, proquazone, protionamide, pyrimethamine, pyrimithate, pyrvinium pamoate, quercetin, quinbolone, quizalofo-ethyl, rafoxanide, rescinnamine, rociverine, ronnel, salen, scarlet red, siccanin, simazine, simetride, simvastatin, sobuzoxane, solan, spironolactone, squalene, stanolone, sucralfate, sulfabenz, sulfaguanole, sulfasalazine, sulfoxide, sulpiride, suxibuzone, talbutal, terguide, testosterone, tetrabromocresol, tetrandrine, thiacetazone, thiocolchicine, thioctic acid, thioquinox, thioridazine, thiram, thymyl N-isoamylcarbamate, tioxidazole, tioxolone, tocopherol, tolciclate, tolnaftate, triclosan, triflusal, triparanol, ursolic acid, valinomycin, verapamil, vinblastine, vitamin A, vitamin D, vitamin E, xenbucin, xylazine, zaltoprofen, and zearalenone.

In one embodiment, the invention provides a hydroxyapatite-targeting, multiarm polymer having the structure:

Formula (Ia)

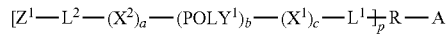

wherein:

A is $—(X^3)_d\text{-}(L^3)_e\text{-}(X^4)_f\text{-POLY}^2\text{-}Z^2$ or $—(X^3)_d\text{-}(L^3)_e\text{-}(X^4)_f\text{-}Z^2$ each $POLY^1$ and $POLY^2$, which may be the same or different, is a water-soluble, non-peptidic polymer;

each $X^1$, $X^2$, $X^3$, and $X^4$, which may be the same or different, is a spacer moiety;

each $L^1$, $L^2$, and $L^3$, which may be the same or different, are linkages;

each $Z^1$, which may be the same or different, is $Z^2$ or a hydroxyapatite-targeting moiety or a multiarm structure comprising 2 to about 10 hydroxyapatite-targeting moieties and optionally including at least one water-soluble, non-peptidic polymer, with the proviso that, when b is zero, at least one $Z^1$ has a multiarm structure comprising one or more polymer arms and with the proviso that at least one $Z^1$ is a hydroxyapatite-targeting moiety;

$Z^2$ is a functional group (e.g., an ionizable functional group), optionally attached to $POLY^2$ through a spacer;

each a, b, c, d, e, and f, which may be the same or different, is either zero or one;

R is a monomeric or oligomeric multiarm core molecule derived from a molecule comprising at least p+1 sites available for attachment; and p is an integer in the range of 2-32.

In certain embodiments, each of $POLY^1$ and $POLY^2$ have a number average molecular weight of less than about 22,000 Da, less than about 15,000 Da, or less than about 8,000 Da. Exemplary polymers for $POLY^1$ and $POLY^2$ include poly (alkylene glycols), poly(olefinic alcohol), poly(vinylpyrrolidone), poly(hydroxyalkylmethacrylamide), poly(hydroxyalkylmethacrylate), poly(saccharides), poly(α-hydroxy acid), poly(acrylic acid), poly(vinyl alcohol), polyphosphazene, polyoxazoline, poly(N-acryloylmorpholine), and copolymers, terpolymers, or mixtures thereof. Examples of the hydroxyapatite-targeting moiety include tetracycline, calcein, bisphosphonates, polyaspartic acid, polyglutamic acid, and aminophosphosugars.

Certain embodiments of the polymer reagents of the invention include at least one hydrolytically or enzymatically cleavable linkage as noted above, such as at the $L^1$, $L^2$, or $L^3$ position. The polymer chains, such as $POLY^1$ and $POLY^2$, can have a segmented structure comprising two to about five water-soluble, non-peptidic polymer segments attached through linkages. For example, one or both of $POLY^1$ and $POLY^2$ can have a structure according to the formula -POLY-L-POLY-, wherein each POLY is a water-soluble, non-peptidic polymer and L is a linkage, which can be enzymatically or hydrolytically cleavable.

In another aspect, the invention provides a hydroxyapatite-targeting, multiarm polymer conjugate comprising the reaction product of the polymer reagent of the invention with a biologically active agent, and having the structure:

Formula (Ib)

wherein B is $—(X^3)_d\text{-}(L^3)_e\text{-}(X^4)_f\text{-POLY}^2\text{-}L^4\text{-Drug}$ or $—(X^3)_d\text{-}(L^3)_n\text{-}(X^4)_f\text{-}L^4\text{-Drug}$, Drug is a residue of a biologically active moiety, $L^4$ is a linkage resulting from reaction of $Z^2$ with a functional group on the biologically active moiety, and $Z^3$ is $L^5$-Drug or a hydroxyapatite-targeting moiety, wherein $L^5$ is a linkage resulting from reaction of $Z^1$, where $Z^1$ is a functional group, with a functional group on the biologically active moiety, with the proviso that at least one $Z^3$ is a hydroxyapatite-targeting moiety.

The core molecule, R, can be any monomeric or oligomeric molecule providing three or more reactive sites for attachment of polymer segments, and will typically include between 3 and about 32 reactive sites, more preferably between 3 and about 25 reactive sites, and most preferably between 3 and about 10 reactive sites (e.g., 3, 4, 5, 6, 7, 8, 9, or 10 reactive sites). Note that the number of reactive sites on the core molecule can be greater than the number of sites actually used for attachment to polymer segments (i.e., the number of reactive sites can be greater than p). The reactive sites comprise terminal functional groups available for reaction with functionalized polymeric segments, and may include more than one type of functional group. For instance, certain di- or tri-peptide core molecules will comprise both one or more carboxylic acid groups and one or more amine groups. As noted above, the R core molecule can be a combination of a polypeptide (e.g., di- or tri-peptide) or disulfide with a polyol to form a multiarm core molecule to which polymer arms can be attached at the site of the hydroxyl groups of the polyol and/or at the site of any free reactive groups on the polypeptide or disulfide. Note that the R core molecule does not have to be preformed prior to attachment of the polymer arms. Instead, the core molecule can be created after polymer arms have been attached to one of the components that will form the ultimate core molecule. For example, polymer arms can be attached to a polyol molecule prior to attachment of two polymer-modified polyol molecules together through a disulfide or di-peptide linker.

A polyol used as the core molecule comprises a plurality of available hydroxyl groups. Depending on the desired number of polymer arms, the polyol will typically comprise 3 to about 25 hydroxyl groups, preferably about 3 to about 22 hydroxyl groups, most preferably about 5 to about 12 hydroxyl groups. Although the spacing between hydroxyl groups will vary from polyol to polyol, there are typically 1 to about 20 atoms, such as carbon atoms, between each hydroxyl group, preferably 1 to about 5. The particular polyol chosen will depend on the desired number of hydroxyl groups needed as attachment sites for the polymer arms. The number average molecular weight of the polyol starting material is typically between about 100 to about 2,000 Da. The polyol typically has a branched structure, meaning one or more carbon atoms in the hydrocarbon core structure of the polyol are covalently attached to three or four atoms selected from carbon atoms and ether-linked oxygen atoms (i.e., oxygen atoms attached to two carbon atoms).

Preferred polyols for use as the core molecule include glycerol oligomers or polymers such as hexaglycerol, pentaerythritol and oligomers or polymers thereof (e.g., dipentaerythritol, tripentaerythritol, and tetrapentaerythritol), and sugar-derived alcohols such as sorbitol, arabanitol, and mannitol. Also, many commercially available polyols containing ionizable groups, such as 2-amino-2-(hydroxymethyl)-1,3-propanediol (TRIS), 2-[bis(2-hydroxyethyl)amino]-2-(hydroxymethyl)-1,3-propanediol, {[2-hydroxy-1,1-bis(hydroxymethyl)ethyl]amino}acetic acid (Tricine), 2-[(3-{[2-hydroxy-1,1-bis(hydroxymethyl)ethyl]amino}propyl)amino]-2-(hydroxymethyl)-1,3-propanediol, 2-{[2-hydroxy-1,1-bis(hydroxymethyl)ethyl]amino}ethanesulfonic acid (TES), 4-{[2-hydroxy-1,1-bis(hydroxymethyl)ethyl]amino}-1-butanesulfonic acid, and 2-[bis(2-hydroxyethyl)amino]-2-(hydroxymethyl)-1,3-propanediol hydrochloride are appropriate starting materials. Typically, polymeric polyols used in the present invention will comprise no more than about 25 monomer units. The structures of dipentaerythritol and tripentaerythritol are provided below along with one of the structures possible for hexaglycerol.

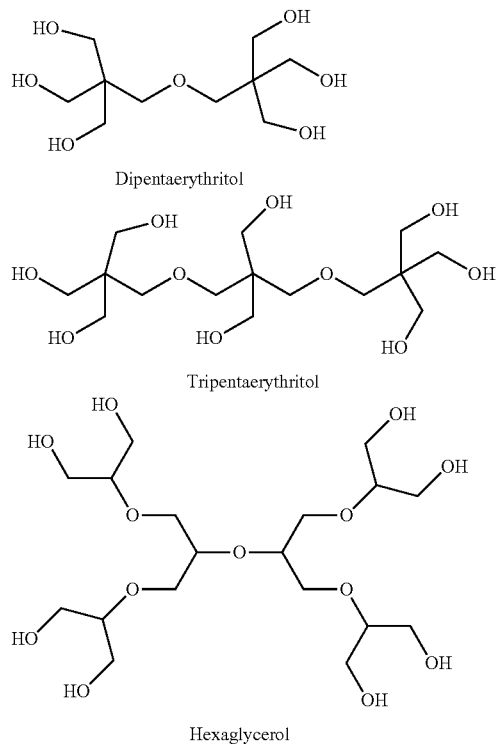

Hydroxypropyl-β-cyclodextrin, which has 21 available hydroxyl groups, is another exemplary polyol. Yet another exemplary polyol is a hyperbranched polyglycerol available from Hyperpolymers GmbH of Freiburg, Germany, which is shown below.

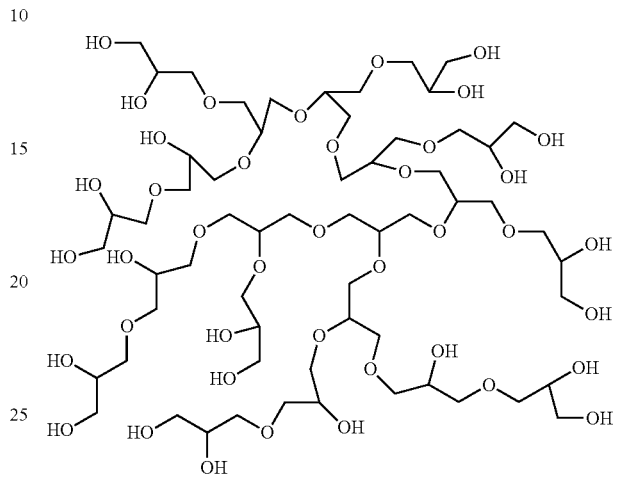

The polyol may include PEG oligomer or polymer segments attached to the polyol core. The polyol starting material is typically in the form of a mixture of products, such as a mixture of polyol oligomers or polymers of different molecular weights or a mixture of ethoxylated polyol structures of different molecule weight, possibly further comprising a residual amount of the original polyol monomeric unit, such as glycerol. However, at least one of the polyols in the starting mixture is typically a branched polyol having at least three available hydroxyl groups according to the formula $R(OH)_p$, wherein R is a branched hydrocarbon, optionally including one or more ether linkages, and p is at least 3, typically 3 to about 25, and preferably 3 to about 10.

Polyols having closely-spaced hydroxyl groups are particularly preferred in certain embodiments of the invention, which facilitate use of cyclic acetal or ketal groups as hydroxyl-protecting groups. A spacing of two or three carbon atoms between hydroxyl groups within the polyol structure enables the formation of certain preferred heterocyclic protecting groups. For example, the close spacing between hydroxyl groups of pentaerythritol oligomers or polymers enable the formation of cyclic acetal or ketal groups using techniques known in the art. The cyclic acetal or ketal groups can be formed by reacting the polyol with an aldehyde reagent, such as a reagent having the formula R'—CHO, wherein R' is alkyl, substituted alkyl, aryl, or substituted aryl, or a ketone reagent (e.g., cyclohexanone). An exemplary aldehyde reagent is benzaldehyde.

By placing a majority of the hydroxyl groups of the polyol in a protected form, the polyol core can be reacted with a reagent comprising the ionizable functional group to produce a plurality of products differentiated by the number of ionizable functional groups present therein. Typically, the reaction will produce a monofunctionalized product, a difunctionalized product, and residual unreacted polyol. An ion exchange chromatography system can be used to separate each product fraction based on difference in charge, thereby allowing purification of the desired monofunctional product. A process for purifying PEG polymer species based on charge differences is set forth in U.S. Patent Application Publication No. 2005/0054816, which is hereby incorporated by reference in its entirety.

The ion exchange column or columns utilized in the purification process can be any ion exchange columns conventionally used to separate a mixture based on charge (Ion Exchange Chromatography. Principles and Method. Pharmacia Biotech 1994; "Chromatography: a laboratory handbook of chromatographic and electrophoretic techniques." Heftman, E (Ed.), Van Nostrand Rheinhold Co., New York, 1975). Each column comprises an ion exchange media and a mobile phase or eluent that passes through the ion exchange media. Ion exchange columns suitable for use in the present invention include POROS® ion exchange media made by Applied Biosystems and SEPHAROSE® ion exchange media made by Pharmacia.

In certain embodiments, each $POLY^1$ is a poly(ethylene glycol) polymer, and R is a disulfide linker, a dipeptide, a tripeptide, or a tetrapeptide, which means the R moiety will include at least one disulfide bond (from the disulfide linker) or amide bond (e.g., the linkage between peptide residues). Preferred R groups include those comprising at least one lysine residue. Suitable disulfide linkers include various linkers comprising an —S—S— bond and a total of 4-25 atoms in chain length, and preferred disulfide molecules have 4-8 functional groups available for attachment of polymer segments. In certain embodiments, each $POLY^1$ and $POLY^2$ is a branched poly(ethylene glycol) polymer.

Polymeric reagent can comprise R moieties derived from a disulfide molecule having the structure:

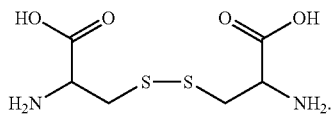

In further embodiments, each $POLY^1$ comprises a poly(ethylene glycol) polymer, and R is comprises at least one peptide residue. The R moiety may further comprise a disulfide bond. In certain embodiments, R comprises at least two lysine residues linked by amide linkages to a linker selected from the group consisting of an aliphatic carbon chain, an aliphatic carbon chain comprising a disulfide bond, and a poly(ethylene glycol) oligomer (e.g., an oligomer having from 1-25 monomer units).

In still further embodiments, each $POLY^1$ comprises a poly(ethylene glycol) polymer and R comprises a non-peptidic moiety comprising at least one disulfide bond and at least two amide bonds. By "non-peptidic" is meant that the R molecule does not include a peptide residue (i.e., the amide and disulfide bonds are not part of a peptide molecule). In this manner, R core molecules can be used that mimic peptidic molecules in structure due to inclusion of amide linkages, but which are not technically peptidic in nature.

Although multiarm structures are most preferred, in another aspect, the invention provides a heterobifunctional, substantially linear, hydroxyapatite-targeting polymer having the structure:

wherein:

each $POLY^1$ and $POLY^2$, which may be the same or different, is a water-soluble, non-peptidic polymer;

each $X^1$, $X^2$, $X^3$, $X^4$, and $X^5$, which may be the same or different, is a spacer moiety;

$L^1$ is a linkage;

each $L^2$ is a hydrolytically or enzymatically cleavable linkage selected from the group consisting of carbamate and amide;

Z is a hydroxyapatite-targeting moiety;

Y is a functional group;

each a, b, c, d, and e, which may be the same or different, is either zero or one; and m is an integer in the range of 1-10.

Exemplary polymer reagents of the invention include the following polymer structures:

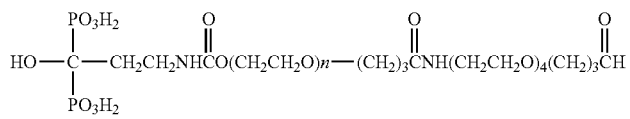

AHPDP-PEG(5K)-Butyraldehyde

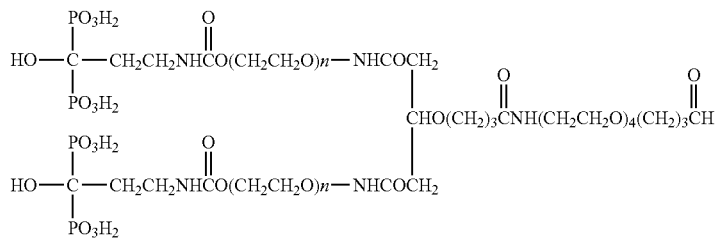

AHPDP-reverse urethane-PEG2(10K)-Butyraldehyde

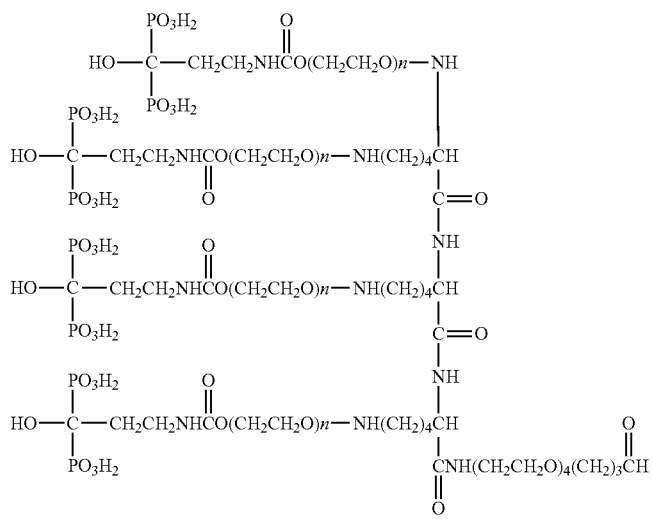

AHPDP-trilysine based-PEG4(20K)-Butyraldehyde

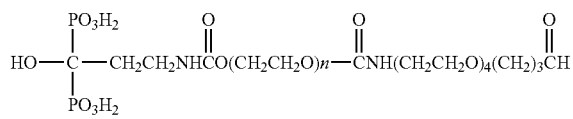

AHPDP-PEG(5K)-Butyraldehyde (2-nd structure)

Example 1 provides an exemplary synthesis route for the first structure noted above. The second structure above is based upon a "PEG2" molecule with a glycerol core, two remote bisphosphonate groups on the PEG chain termini, and a site for drug attachment through the butanoic acid functional group. To construct this molecule, one can use a benzyl-capped PEG (b-PEG), rather than a typical methoxy-capped PEG (m-PEG). Then, in an appropriate processing step, the benzyl groups can be removed by hydrogenolysis and, through a series of steps, the bisphosphonate functions can be added. Example 2 illustrates a possible synthetic route to molecules of this type. Example 3 provides an exemplary synthesis for the trilysine-based polymer reagent noted above.

The method of forming a hydroxyapatite-targeting multi-arm polymer of the invention can vary. Reaction Scheme 1 below illustrates one method of constructing a six-arm polyol, based on pentaerythritol, having an ester as the ionizable reactive arm (protected carboxylic acid). In this example, the linker $L_3$ is a multifunctional linker, such as lysine.

Reaction Scheme 1
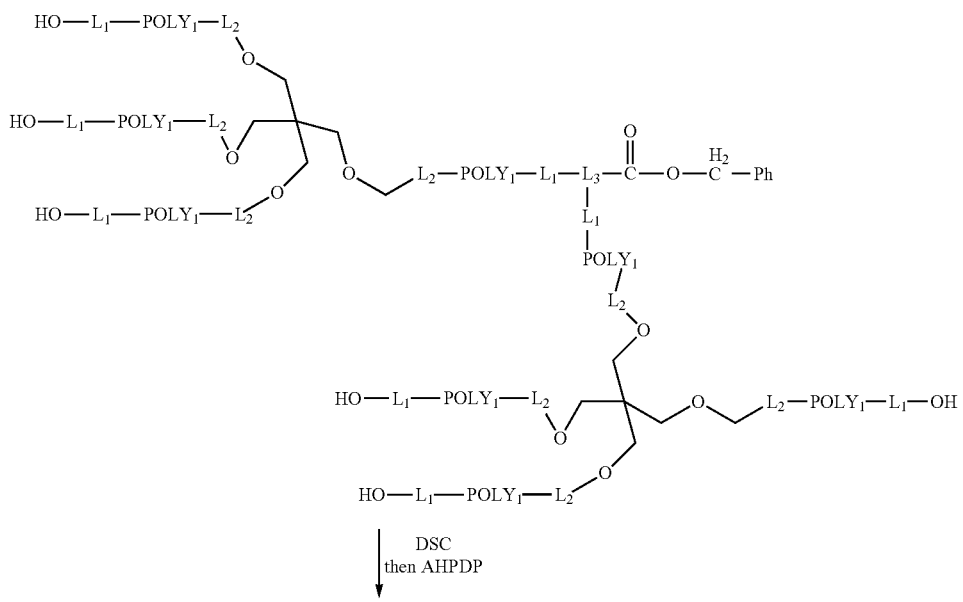
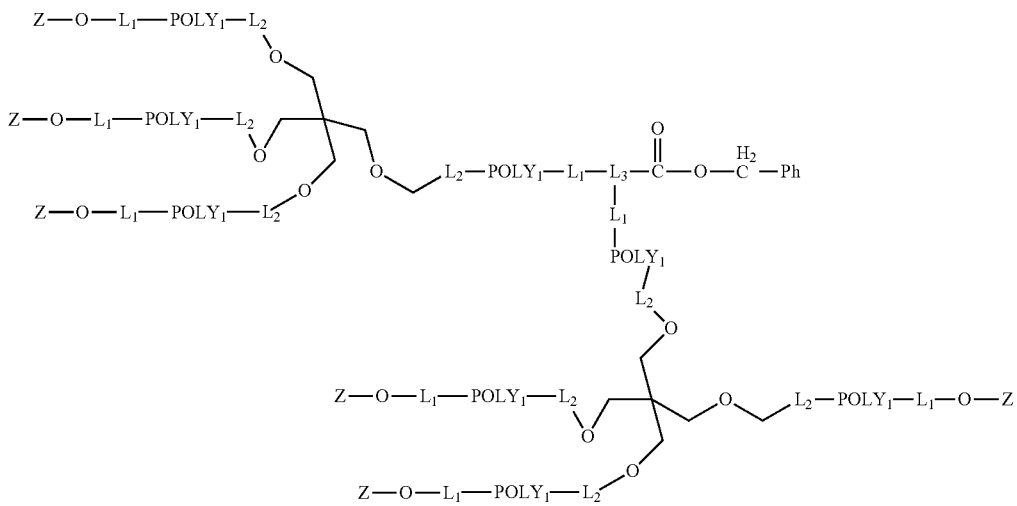
DSC = Disuccinimidyl carbonate
AHPDP = 3-amino-1-hydroxy-1,1-diphosphonic acid
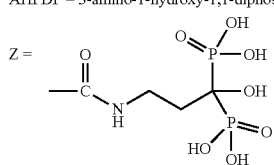
Reaction Scheme 2 below shows how the above generalized structure of Reaction Scheme 1 is deprotected (by hydrogenolysis of the benzyl ester) and then activated for subsequent reaction with an amine-terminal therapeutic agent.

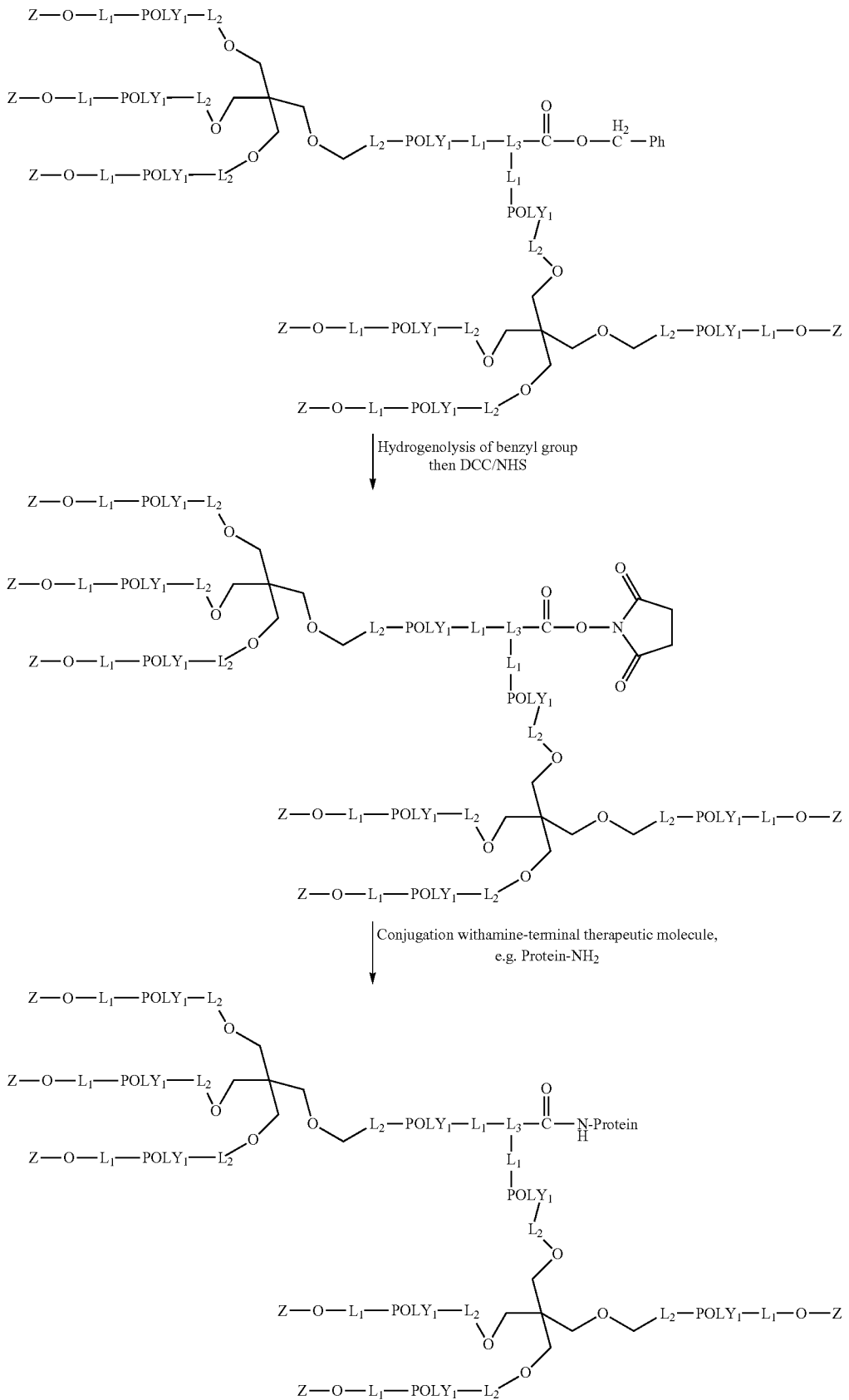

-continued

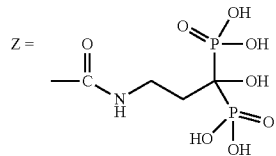 [SMILES: CC(=O)NCCC(O)(P(=O)(O)O)P(=O)(O)O]

Reaction Scheme 3 below shows a method of attaching a bone-targeting moiety to the termini of a polymer having a lysine core and a carboxylic acid group as the ionizable reactive arm. As shown, the trityl groups are subjected to hydrogenolysis, followed by esterification of the acid group to form a protected acid, and then reaction of the termini with a bone-targeting agent, which in this case is AHPDP (a derivative of 3-amino-1-hydroxypropane-1,1-diphosphonic acid). The resulting polymeric species, in Reaction Scheme 3 below, can be subjected to hydrogenolysis to remove the benzyl ester group. Then, reaction with DCC/NHS, following conditions similar to those used in U.S. Pat. No. 6,436,386 B1, which is incorporated by reference, can convert this bone-targeting polymer into an active ester reagent (NHS ester) that can be used to conjugate therapeutic agents through an available amine group on the therapeutic agent, e.g., an N-terminal lysine.

As indicated above, certain homo-oligomers of amino acids having a free carboxyl group, such as polyaspartic acid or polyglutamic acid, have a good binding capacity for hydroxyapatite. Therefore, an alternate structure for a bone-targeting polymer can be prepared using this type of polypeptide group as a pendant group. Shown in the scheme below (Reaction Scheme 4) is a way that a commercially available heterobifunctional PEG derivative can be reacted with a polyaspartic acid, which is known in the art. The product, which still has both the amine and terminal carboxylic acids blocked, can be further manipulated to deblock the amine group. This intermediate can be used directly in forming a multiarm reagent (see Reaction Scheme 5, for example) or it can be further manipulated to form an active ester, which can be converted into a different multiarm reagent, which is not shown.

Reaction Scheme 3

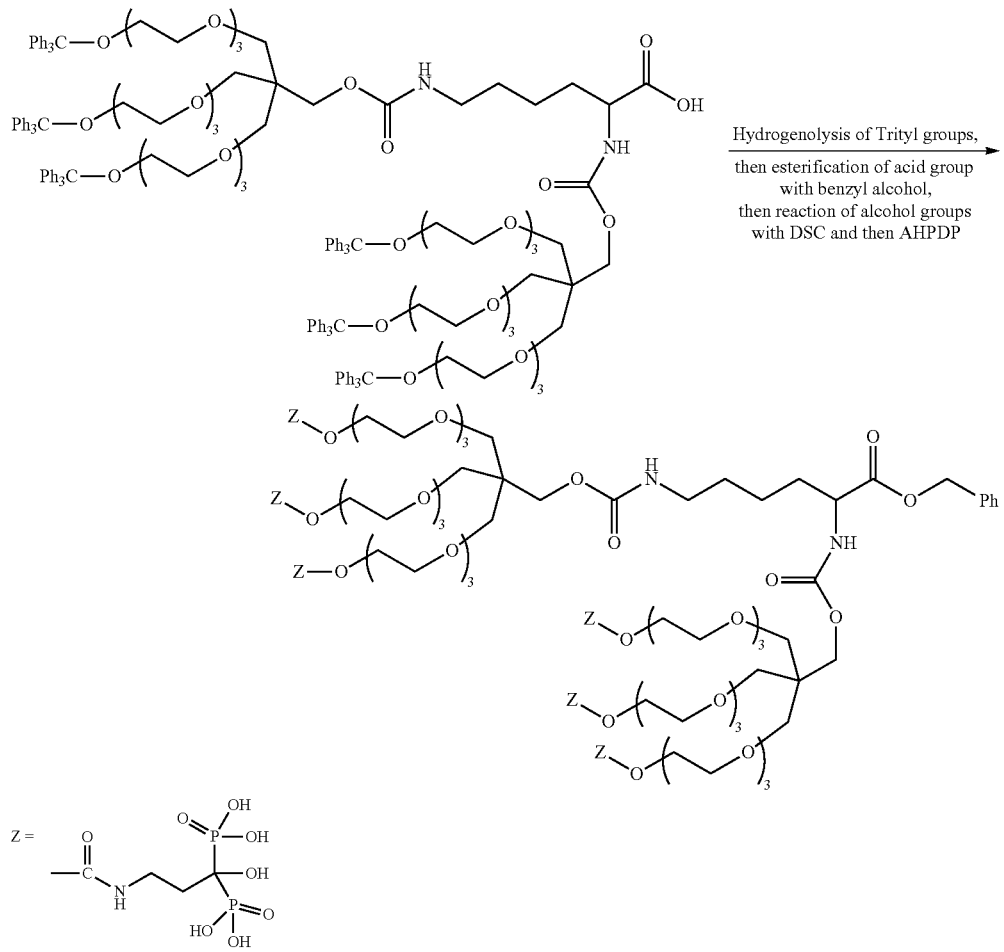

Reaction Scheme 4
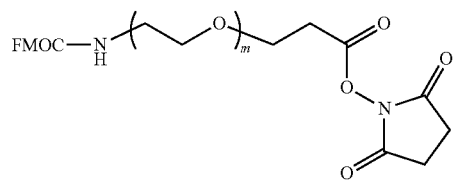
n = typically 3-12
m = typically 3-90
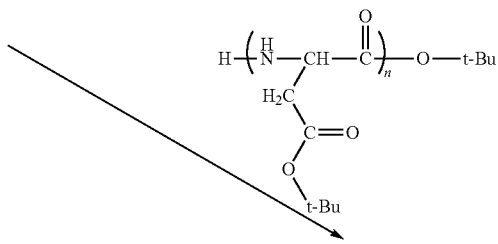
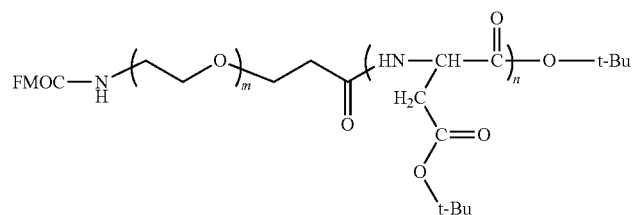
Deprotect FMOC ↓
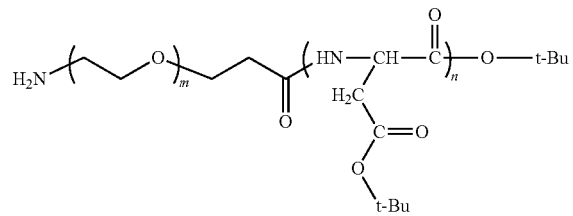
↓ then DCC/NHS
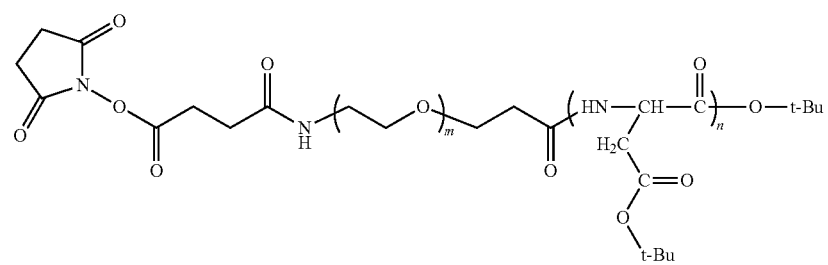

Reaction Scheme 5 below illustrates the formation of amine- and acid-protected intermediates used in preparing a polypeptide-containing bone-targeting multiarm polymeric reagent.

Reaction Scheme 5

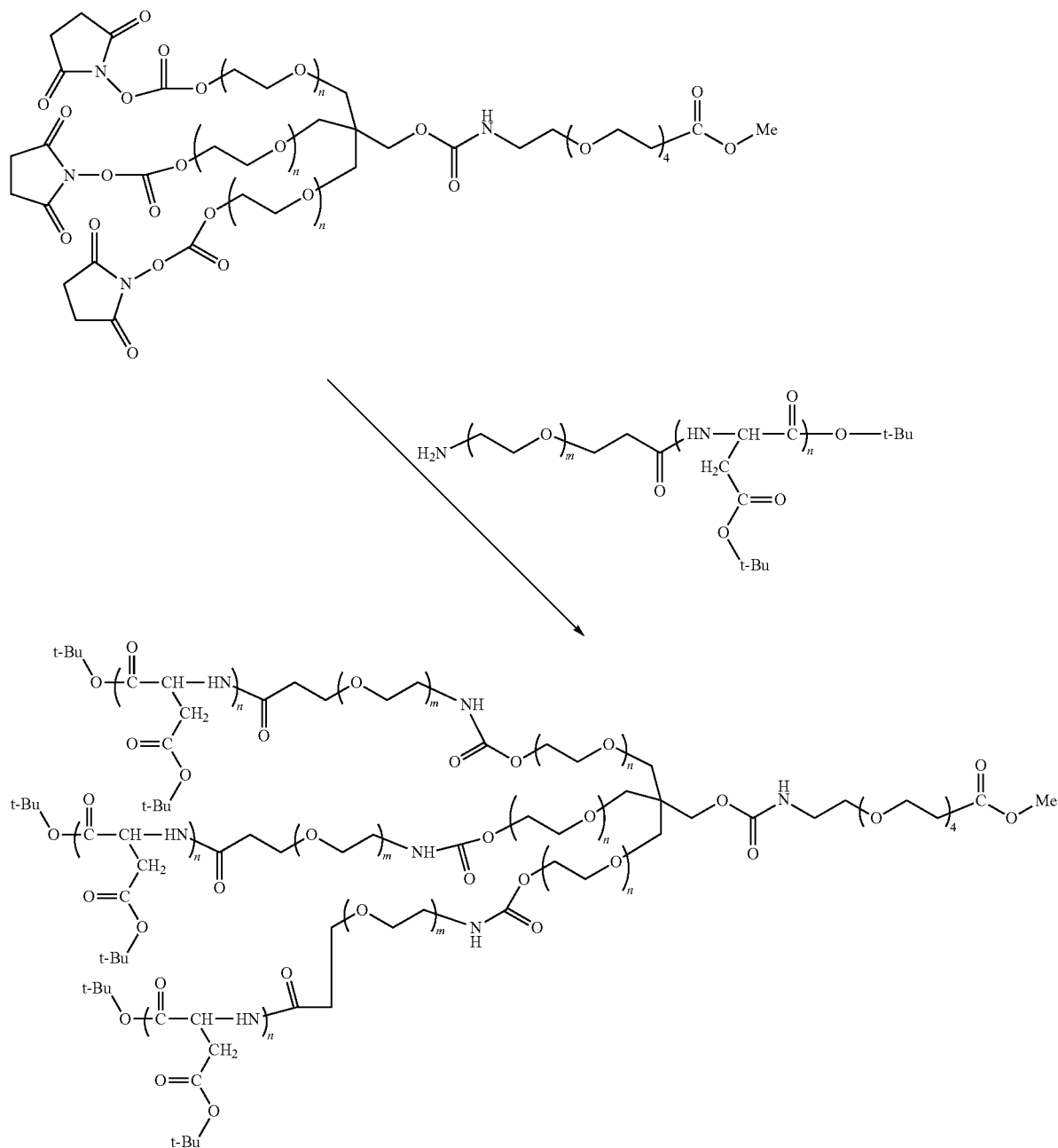

In Reaction Scheme 6 below, the methyl ester intermediate from Reaction Scheme 5 is deprotected by base hydrolysis, which will not affect the t-butyl esters. The resulting carboxylic acid is then esterified to an active ester with dicyclohexylcarbodiimide and N-hydroxysuccinimide. Reaction with an amine-bearing reagent for forming a maleimide gives the polymeric reagent bearing a maleimide group and still having the carboxylic acid esters on the polypeptide moieties. A mild acid hydrolysis will remove the protecting groups giving a reagent that is reactive toward thiol-containing therapeutic agents.
Reaction Scheme 6
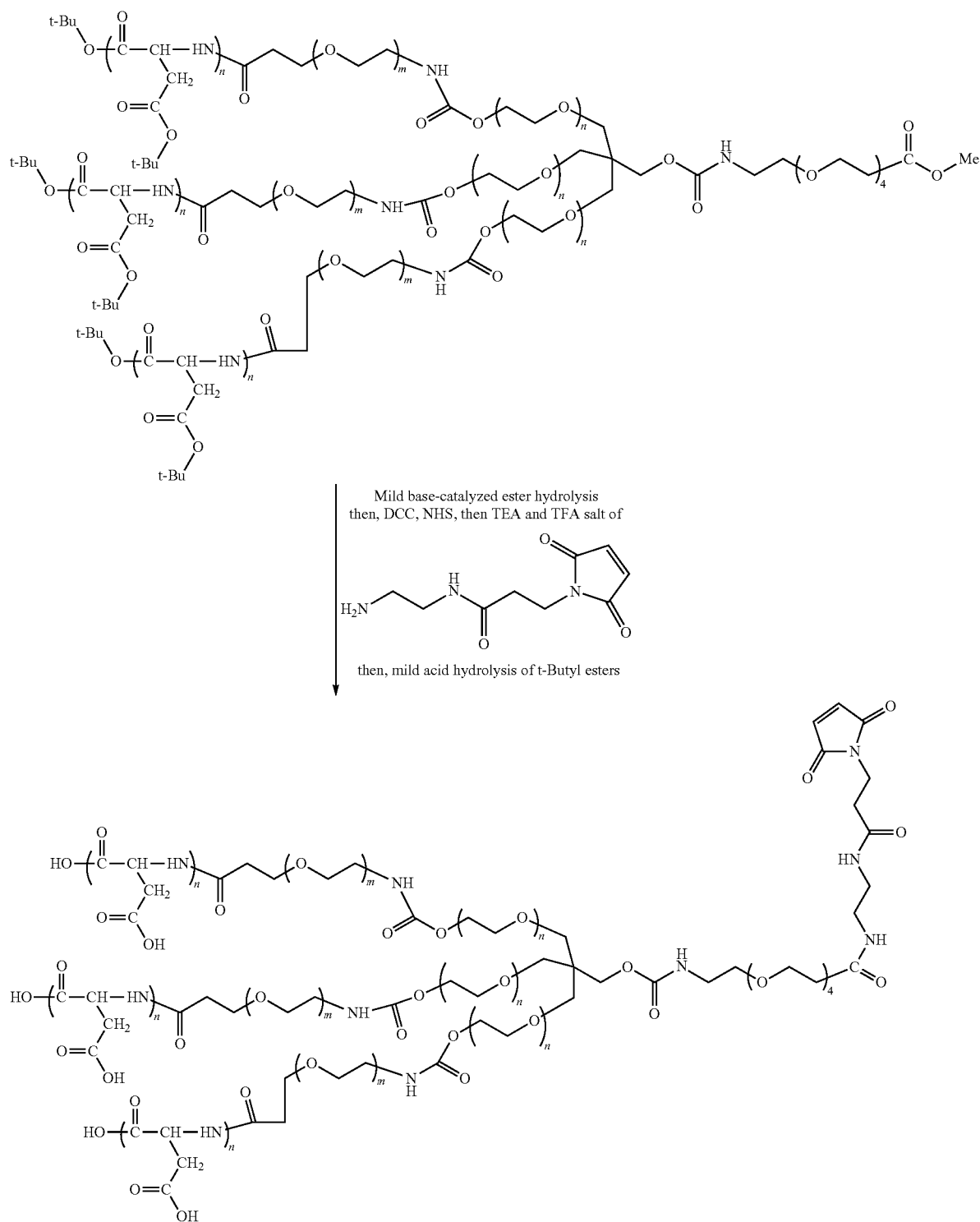
In Reaction Scheme 7 below, the conjugation with the reagent above is illustrated with a therapeutic agent, which happens to be a polypeptide, bearing a thiol group.

Reaction Scheme 7

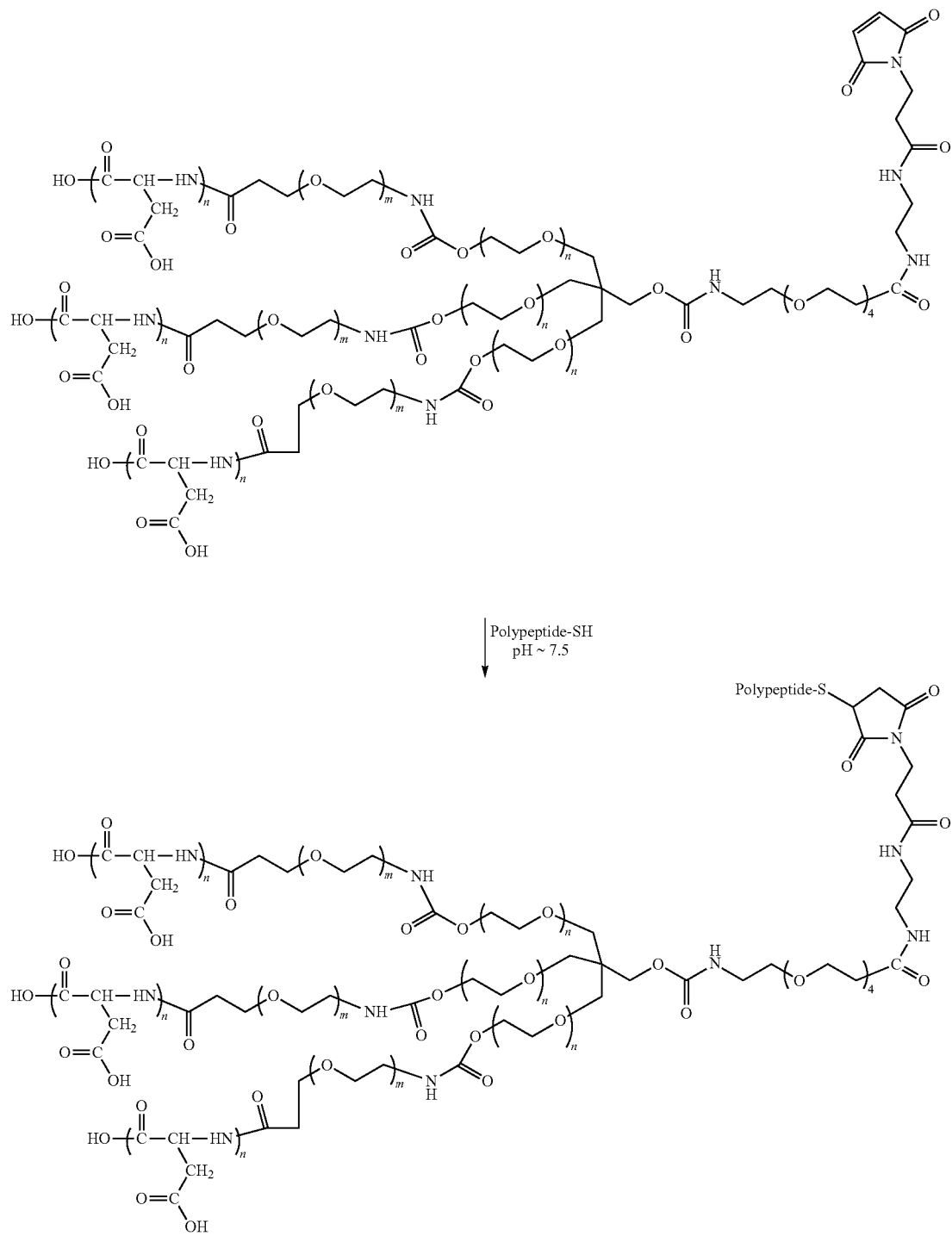

The invention includes polymer reagents and conjugates made therefrom that are designed to act as a prodrug and release the biologically active moiety at the bone site. In this case, a degradable functional group is added at the site where conjugation to the drug occurs. Degradable functional groups of the phenolate or FMOC type can readily be incorporated into this type of molecule and thus are hereby included as a feature of this class of reagent.

In Reaction Scheme 8 below is shown an example of a polymeric reagent containing a tripeptide link that can be enzymatically cleaved in vivo to allow for the polymer to clear as smaller fragments. Using commercially available trilysine as a core tripeptide, the free amine groups are reacted with a benzyl protected active carbonate PEG (b-PEG-BTC). This leads to formation of a four-arm polymer with the remote termini protected with a removable benzyl group. Note that the polymer has a carboxylic acid group that can be used to purify the polymer and also to activate for connection to a drug molecule.

In an alternate process, a four-arm structure can be derived from use of the monoblocked (ester) disulfide linked dipeptide Lys-Cys, i.e. shown below.

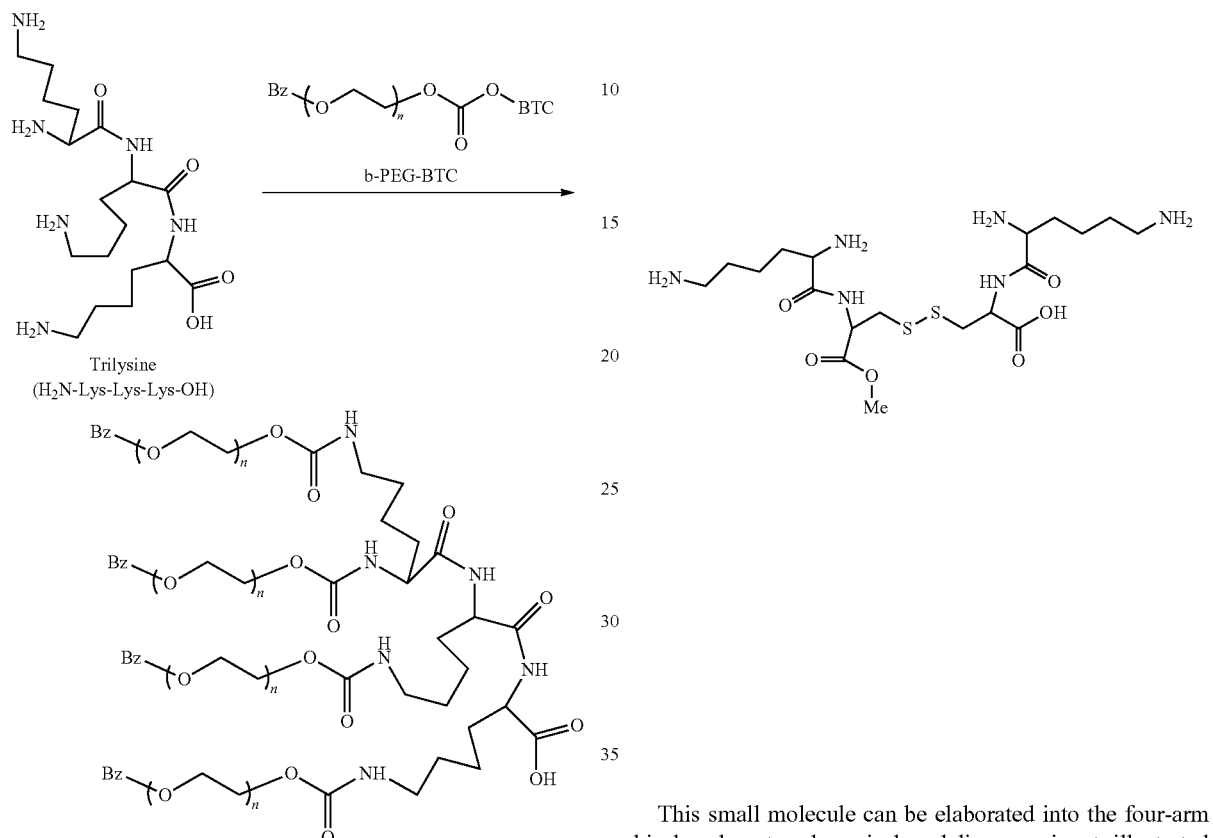

Completion of a series of processing steps to the product of Reaction Scheme 8 allows addition of the bone-targeting functionality and the drug leading to the four-arm bisphosphonate set forth below.

This small molecule can be elaborated into the four-arm bisphosphonate polymeric drug delivery conjugate illustrated below. The advantage of using the segmented polymeric species resides in the ability of these polymers to break down, through enzyme or intracellular chemical action, into smaller, linear fragments that will clear from the body more quickly than stable multiarm molecules like those based on certain polyols.

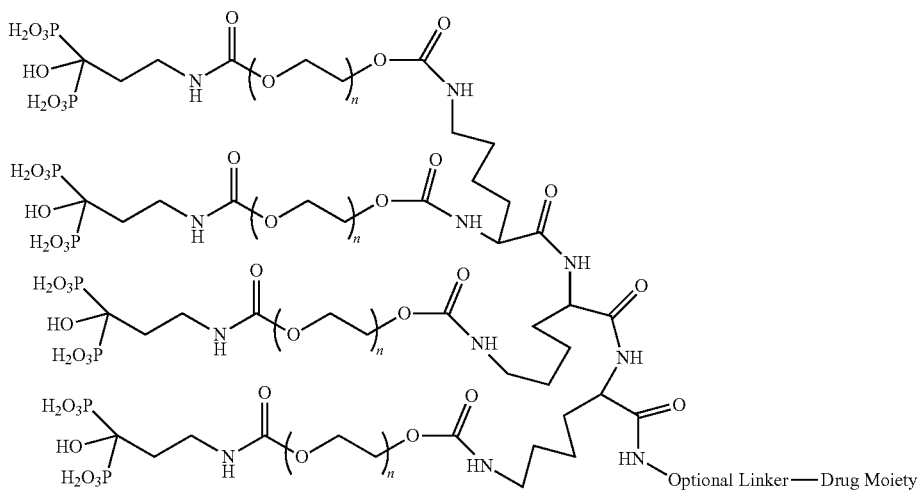

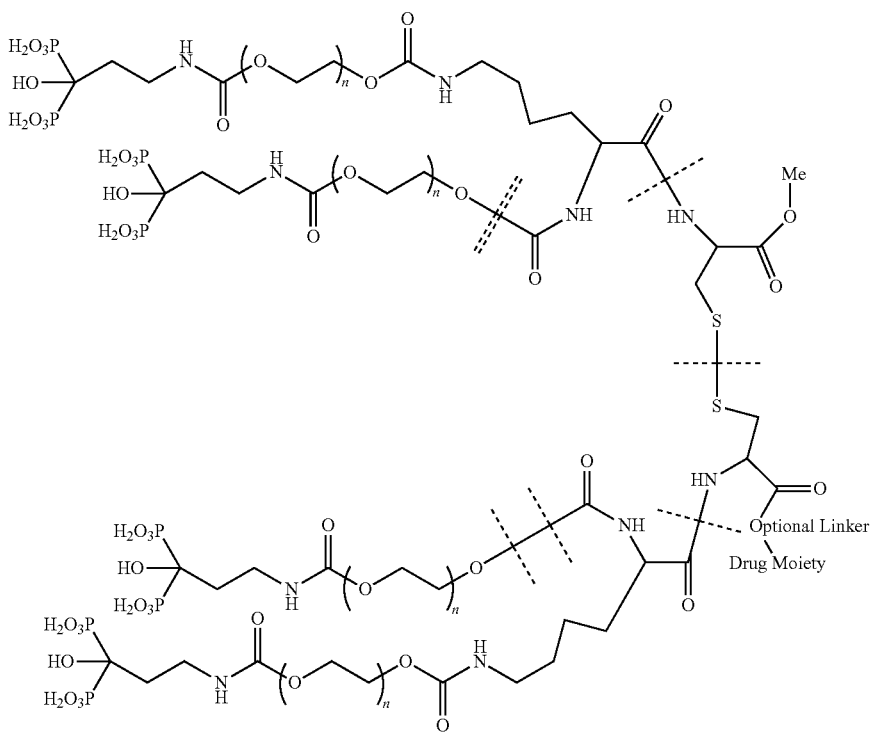

Following pathways known in the art, the molecule above could cleave at the bonding sites designated by the dotted lines. The single dotted lines are sites where enzymatic or intracellular chemical cleavage is likely and the double dotted lines represent sites where depegylation may occur through a chemical process that involves a neighboring amide group (Guiotto et al, *Biorg. Med. Chem.* 2004, 12, 5031-5037). Disulfide bonds in water soluble polymer-bound drug molecules are known to undergo cleavage in serum or in the cell by agents like glutathione (Zalipsky et al *Bioconj. Chem.* 1999, 10, 703-707; U.S. Pat. No. 6,342,244B1; US Pat Appl. 2005/0170508A1; Huang et al, *Bioconj Chem.* 1998, 9, 612-617). Enzymatic cleavage of peptide bonds has also been reported with water soluble polymers (Ulbrich et al *Makromol. Chem.* 1986, 187, 1131-1144; Suzawa et al, *J. Controlled Rel.* 2000, 69, 27-41; Suzawa et al U.S. Pat. No. 6,103,236).

The use of segmented polymers having bisphosphonate bone-targeting groups may be important when a high molecular weight polymer is desired to enhance delivery and retention of the conjugate until bone targeting has been achieved. Then, segment cleavage would allow clearance of the polymer fragments as they would all be of lower molecular weight and generally linear polymers with linkers.

In addition to the polymer reagents, conjugates made therefrom, and methods of synthesis described above, the invention further includes methods of using the polymer conjugates therapeutically to treat various conditions and disease states that would benefit from the targeted delivery of a biologically active agent to the surface of bone. Exemplary conditions to be treated include bone cancer, infections of bone tissue, age-induced degradation of bone tissue, bone defects caused by trauma, and the like. The choice of administration route, biologically active moiety, and dosage range can be readily determined by the clinician and will vary based on numerous factors including the condition to be treated, the condition of the patient, the severity of the injury or disease, and the like.

All articles, books, patents, patent publications and other publications referenced herein are hereby incorporated by reference in their entireties.

EXPERIMENTAL

It is to be understood that while the invention has been described in conjunction with certain preferred specific embodiments thereof, the foregoing description as well as the example that follows are intended to illustrate and not limit the scope of the invention. Other aspects, advantages and modifications within the scope of the invention will be apparent to those skilled in the art to which the invention pertains. For example, in certain applications, it may be desirable to utilize a polymeric reagent according to any of the above formulas wherein all linkages therein are stable rather than degradable.

All PEG reagents referred to in the appended example are commercially available unless otherwise indicated, e.g., from Nektar Therapeutics, Huntsville, Ala. All $^1$HNMR data was generated by a 300 or 400 MHz NMR spectrometer manufactured by Bruker. High Performance Liquid Chromatography (HPLC) was performed using Agilent 1100 HPLC system (Agilent), gel permeation or ion exchange column, aqueous phosphate buffer as a mobile phase, and refractive index (RI) detector.

Example 1

I. PEG (5,000 Da)-α-hydroxy-ω-butanoic acid, methyl ester

To a solution of PEG (5,000)-α-hydroxy-ω-butanoic acid (70 g, 0.0140 moles) (Nektar Therapeutics) in anhydrous methanol (400 ml) was added concentrated sulfuric acid (8.0 ml) followed by stirring of the mixture for 3 h at room temperature. NaHCO$_3$ (8% aqueous solution) was added to adjust the pH of the mixture to 7.0. Methanol was distilled off under reduced pressure and the product was extracted with CH$_2$Cl$_2$ (2×350 ml). The extract was dried (MgSO$_4$) and the solvent was distilled off under reduced pressure. Yield 60 g.

NMR (d$_6$-DMSO): 1.72 ppm (m, —C<u>H</u>$_2$CH$_2$COO—, 2H), 2.34 ppm (t, —CH$_2$COO—, 2H), 3.51 ppm (s, PEG backbone), 4.57 ppm (t, —OH, 1H), 3.58 ppm (s, CH$_3$O—, 3H).

II. PEG (5,000 Da)-α-succinimidyl carbonate-ω-butanoic acid, methyl ester

To a solution of PEG (5,000 Da)-α-hydroxy-ω-butanoic acid, methyl ester (60 g, 0.0120 moles) in acetonitrile (300 ml), pyridine (1.60 ml) and disuccinimidyl carbonate (3.92 g) were added and the reaction mixture was stirred overnight at room temperature under argon atmosphere. Next the mixture was filtered and solvent was evaporated to dryness. The crude product was dissolved in methylene chloride and precipitated with isopropyl alcohol. The wet product was dried under reduced pressure. Yield 57 g.

NMR (d$_6$-DMSO): 1.72 ppm (m, —C<u>H</u>$_2$CH$_2$COO—, 2H), 2.34 ppm (t, —CH$_2$COO—, 2H), 2.81 ppm (s, —CH$_2$CH$_2$— (succinimide), 4H), 3.51 ppm (s, PEG backbone), 3.58 ppm (s, —CH$_3$O—, 3H), 4.45 ppm (m, —CH$_2$—O(C=O)—, 2H).

III. PEG (5,000 Da)-α-AHPDP-ω-butanoic acid

To a solution of PEG (5,000 Da)-α-succinimidyl carbonate-ω-butanoic acid, methyl ester (40 g, 0.0080 moles) in acetonitrile (400 ml), 3-amino-1-hydroxypropane-1,1-diphosphonic acid, ditetrabutylammonium salt (AHPDP-2Bu$_4$N) (6.2 g) and triethylamine (2.4 ml) were added and the reaction mixture was stirred overnight at room temperature under argon atmosphere. Next solvent was evaporated to dryness. The crude product was dissolved in DI water (400 ml) and the pH of the solution was adjusted to 12.0 with 1M sodium hydroxide. The solution was stirred 2 h keeping the pH at 12 by periodic addition of 1M sodium hydroxide then it was filtered through Amberlite IR 120 (plus) column (200 ml). From the filtrate, water was distilled off under reduced pressure. The wet product was dissolved in methylene chloride (600 ml) then the solvent was distilled off. Finally the product was dried under reduced pressure. Yield 35 g.

NMR (d$_6$-DMSO): 1.72 ppm (m, —C<u>H</u>$_2$CH$_2$COO—, 2H), 2.02 ppm (m, —CH$_2$— (AHPDP), 2H), 2.34 ppm (t, —CH$_2$COO—, 2H), 3.51 ppm (s, PEG backbone), 4.03 ppm (m, —CH$_2$—O(C=O)—, 2H), 7.11 ppm (t, —(C=O)NH—, 1H).

IV. PEG (5,000)-α-AHPDP-ω-butanoic acid, N-hydroxysuccinimide ester

To a solution of PEG (5,000 Da)-α-AHPDP-ω-butanoic acid (30 g, 0.0060 equivalents) in anhydrous methylene chloride (300 ml), N-hydroxysuccinimide (0.83 g, 0.0072 moles) was added following by 1,3-dicyclohexylcarbodiimide (1.0 M solution in methylene chloride, 7.2 ml, 0.0072 moles). The reaction mixture was stirred overnight at room temperature under an argon atmosphere. Next the mixture was filtered and solvent was evaporated to dryness. The crude product was dissolved in methylene chloride and precipitated with isopropyl alcohol. Finally the product was dried under reduced pressure. Yield 27 g.

NMR (d$_6$-DMSO): 1.84 ppm (m, —C<u>H</u>$_2$CH$_2$COO—, 2H), 2.02 ppm (m, —CH$_2$— (AHPDP), 2H), 2.71 ppm (t, —CH$_2$COO—, 2H), 2.81 ppm (s, —CH$_2$CH$_2$— (succinimide), 4H), 3.51 ppm (s, PEG backbone), 4.03 ppm (m, —CH$_2$—O(C=O)—, 2H), 7.11 ppm (t, —(C=O)—NH—, 1H).

V. PEG (5,000)-α-AHPDP-ω-butyraldehyde diethyl acetal

To a solution of PEG (5,000 Da)-α-AHPDP-ω-butanoic acid, N-hydroxysuccinimide ester (25 g, 0.0050 equivalents) in anhydrous methylene chloride (250 ml), tetra(ethylene glycol)-α-amino-ω-butyraldehyde, diethyl acetal (Nektar Therapeutics; 2.0 g, 0.0059 moles) was added following by triethylamine (1.70 ml). The reaction mixture was stirred overnight at room temperature under argon atmosphere. Next the mixture was filtered and solvent was evaporated to dryness. The crude product was dissolved in methylene chloride and precipitated with isopropyl alcohol. Finally the product was dried under reduced pressure. Yield 22 g.

NMR (d$_6$-DMSO): 1.10 ppm (t, CH$_3$—C, 6H), 1.51 ppm (m, C—CH$_2$—CH$_2$—,butyraldehyde, 4H), 1.72 ppm (m, —C<u>H</u>$_2$CH$_2$COO—, 2H), 2.02 ppm (m, —CH$_2$— (AHPDP), 2H), 2.10 ppm (t, —CH$_2$COO—, 2H), 3.51 ppm (s, PEG backbone), 4.03 ppm (m, —CH$_2$—O(C=O)—, 2H), 4.46 ppm (t, —CH—, acetal, 1H), 7.11 ppm (t, —(C=O)—NH—, 1H).

VI. PEG (5,000)-α-AHPDP-ω-butyraldehyde

PEG (5,000)-α-AHPDP-ω-butyraldehyde diethyl acetal (20 g) was dissolved in 300 ml water and the pH of the solution was adjusted to 2.5 with diluted phosphoric acid. The solution was stirred 3 hours at room temperature. Next 0.5M sodium hydroxide was used to adjust the pH of the solution to 7. The product was extracted with methylene chloride and precipitated with diethyl ether. Finally the product was dried under reduced pressure. Yield 17.5 g.

NMR (d$_6$-DMSO): 1.75 ppm (m, —C<u>H</u>$_2$CH$_2$CHO, 2H and —C<u>H</u>$_2$CH$_2$COO—, 2H), 2.02 ppm (m, —CH$_2$— (AHPDP), 2H), 2.10 ppm (t, —CH$_2$COO—, 2H), 2.44 ppm (dt, —CH$_2$CHO, 2H), 3.51 ppm (s, PEG backbone), 4.03 ppm (m, —CH$_2$O(C=O)—, 2H), 7.11 ppm (t, —(C=O)—NH—, 1H), 9.66 ppm (t, —CHO, 1H).

Example 2

I. Preparation of a Glycerol-Based Precursor Molecule

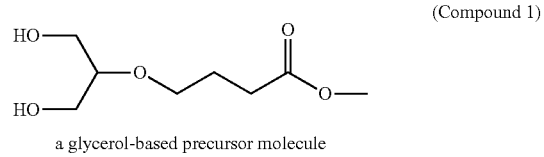

(Compound 1)

a glycerol-based precursor molecule

A solution of cis-1,3-O-Benzylideneglycerol (7.2 g, 0.040 moles) (Sigma-Aldrich Corporation, St. Louis, Mo.) in toluene (100 ml) was azetropically dried by distilling off toluene. The dried compound was dissolved in anhydrous toluene (100 ml) and 1.0M solution of potassium tert-butoxide in tert-butanol (60 ml, 0.060 moles) and 1-(3-bromopropyl)-4-methyl-2,6,7-trioxabicyclo[2,2,2]octane (14.0 g, 0.0558 moles) were added and the mixture was stirred overnight at 100° C. under argon atmosphere. The mixture was filtered and the solvent was distilled off under reduced pressure giving 15.7 g of solid product (Compound 2). NMR (d$_6$-DMSO): 0.74 ppm (s, 3H), 1.61 ppm (m, 4H), 1.88 ppm (m, 2H), 3.44 ppm (t, 2H), 3.81 ppm (s, 6H), 4.05 ppm (m, 4H), 5.55 ppm (s, 1H), 7.37 ppm (m, 5H).

Schematically, the reaction is represented as follows:

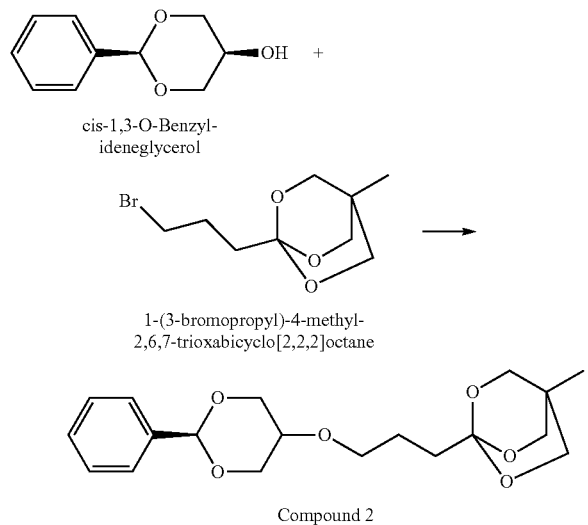

Hydrolysis of Compound 2.

Compound 2 (15.0 g) was dissolved in a mixture of acetonitrile (150 ml) and distilled water (35 ml). Next, a 10% solution of $H_3PO_4$ was added to adjust the pH to 4.5. The mixture was stirred for 1 hour at pH=4.5. NaCl (2 g) was added and the pH was adjusted to 7.5. The product was extracted with $CH_2Cl_2$ (600 and 150 ml).

The extract was dried ($MgSO_4$) and the solvent was distilled off under reduced pressure to give a solid product (Compound 3). The yield was determined to be 14.2 g.

NMR ($d_6$-DMSO): 0.78 ppm (s, 3H), 1.79 ppm (m, 2H), 2.41 ppm (t, 2H), 3.25 ppm (m, 6H), 3.49 ppm (t, 2H), 4.05 ppm (m, 4H), 4.48 ppm (t, 3H), 5.56 ppm (s, 1H), 7.37 ppm (m, 5H).

Schematically, the reaction is represented as follows:

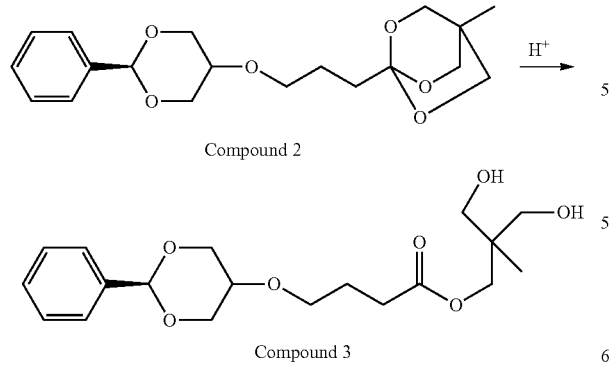

Compound 3 (14.2 g) was dissolved in a mixture of acetonitrile (80 ml) and distilled water (80 ml). Next, a 6% solution of NaOH was added to adjust the pH to 12.5. The solution was stirred for 5.5 hours at pH ranging from 12.3-12.8, which was maintained by periodical additions of a 6% solution of NaOH. NaCl (5 g) was added and the pH was adjusted to 7.5 with 5% $H_3PO_4$. The non-acidic impurities were extracted with $CH_2Cl_2$ (two treatments, a first using 300 ml and a second using 200 ml). The pH of the solution was adjusted to 3.0 with $H_3PO_4$ and the product was extracted with $CH_2Cl_2$ (two treatments, a first using 200 ml and a second using 100 ml).

The extract was dried ($MgSO_4$) and the solvent was distilled off under reduced pressure. The resulting product (Compound 4) had a yield of 8.7 g.

NMR ($d_6$-DMSO): 1.76 ppm (m, 2H), 2.31 ppm (t, 2H), 3.46 ppm (t, 2H), 4.05 ppm (m, 4H), 5.56 ppm (s, 1H), 7.37 ppm (m, 5H).

Schematically, the reaction is represented as follows:

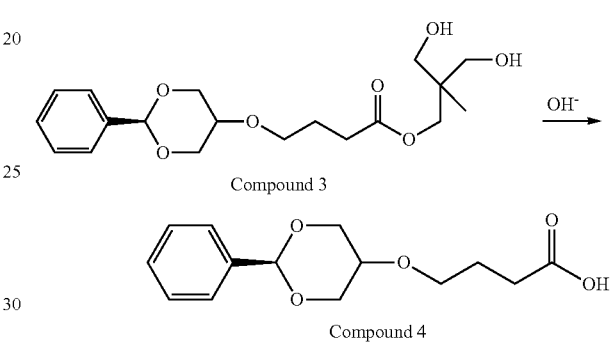

Compound 4 (8.0 g) was dissolved in anhydrous methanol (120 ml) and upon dissolution, concentrated $H_2SO_4$ (1.6 ml) was added. The solution was stirred for 4 hours at room temperature. $NaHCO_3$ (8% solution) was added to adjust the pH of the mixture to 7.5. The product was extracted with $CH_2Cl_2$ (two treatments, each using 100 ml).

The extract was dried ($MgSO_4$) and volatile compounds were distilled off under reduced pressure (0.05 mm Hg) at 60° C. The resulting product (Compound 1) had a yield of 4.8 g.

NMR ($d_6$-DMSO): 1.72 ppm (m, 2H), 2.37 ppm (t, 2H), 3.20 ppm (m, 1H), 3.42 ppm (bm, 4H), 3.49 ppm (t, 2H), 3.59 ppm (s, 3H), 4.46 ppm (t, 2H).

Schematically, the reaction is represented as follows:

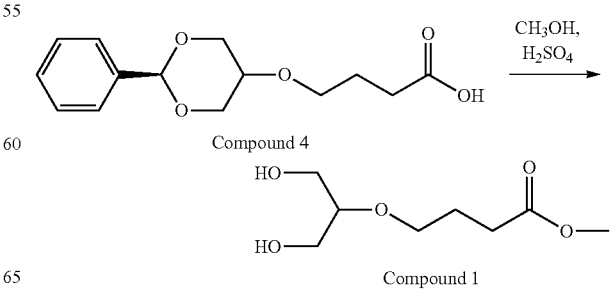

II. Preparation of "HO-PEG2$_{(20K)}$-Butanoic Acid, N-Hydroxysuccinimide Ester"

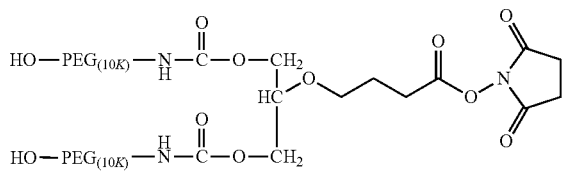

(wherein HO-PEG$_{10K}$ designates a PEG having a molecular weight of 10,000 Daltons) "HO-PEG2$_{(20K)}$-Butanoic Acid, N-Hydroxysuccinimide Ester"

Activation of the Hydroxyl Groups in the Precursor Molecule

Compound 1 (2.0 g, 0.0208 equivalents) was dissolved in anhydrous acetonitrile (50 ml) and anhydrous pyridine (2.2 ml, 0.272 mole) and N,N-disuccinimidyl carbonate (5.86 g, 0.0229 mole, DSC) were added. The solution was stirred overnight at room temperature under argon atmosphere. Next, the mixture was filtered and the solvent was distilled off. The crude product was dissolved in CH$_2$Cl$_2$ (50 ml) and washed with a 5% H$_3$PO$_4$ solution. The solution was then dried (MgSO$_4$), and the solvent was distilled off. The resulting product (Compound 5) had a yield of 2.8 g.

NMR (d$_6$-DMSO): 1.76 ppm (m, 2H), 2.35 ppm (t, 2H), 2.82 ppm (s, 8H), 3.56 ppm (t, 2H), 3.58 ppm (s, 3H), 3.96 ppm (m, 1H), 4.37 ppm (m, 2H), 4.52 ppm (m, 2H).

Schematically, the reaction is represented as follows:

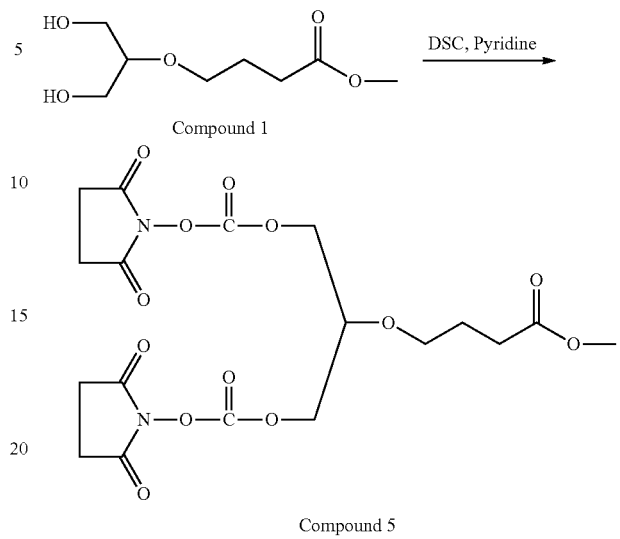

Coupling the Activated Precursor with an Amine-Containing Water-Soluble Polymer

To a mixture of Benzyloxy-PEG$_{(5K)}$-amine (BzO-PEG$_{(5K)}$-amine) (20 g, 0.0040 mole) (Nektar Therapeutics, Huntsville, Ala.), methylene chloride (200 ml), and triethylamine (1.4 ml), Compound 5 (0.901 g, 0.0038 equivalents) was added. The mixture was stirred overnight at room temperature under argon atmosphere. Next, the solvent was distilled off under reduced pressure.

Schematically, the reaction is represented as follows:

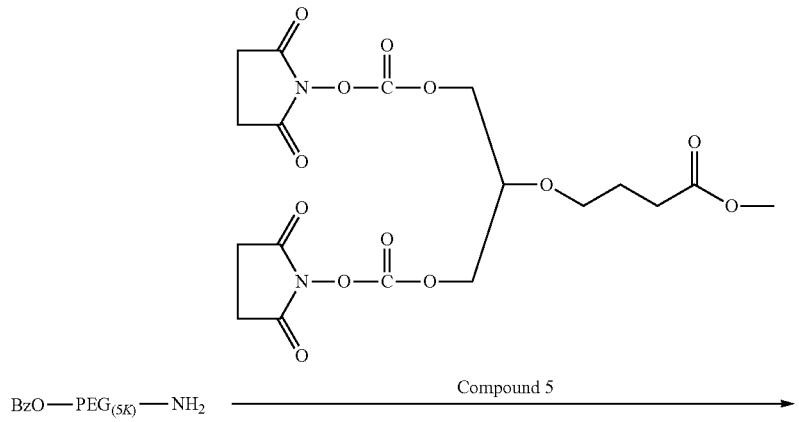

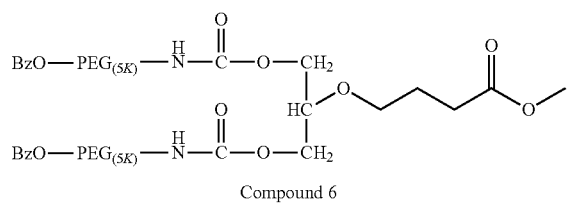

Deprotecting Step and Chromatographic Purification of BzO-PEG2$_{(20K)}$-Butanoic Acid The obtained Compound 6 (herein referred to as BzO-PEG2$_{(20K)}$-butanoic acid, methyl ester) was dissolved in 400 ml of distilled water and the pH of the solution was adjusted to 12.2 with a 0.5M NaOH solution. The solution was stirred for 3 hours at a pH in a range of 12.0-12.2. Next, NaCl (20 g) was added and the pH was adjusted to 3.0 with a 5% $H_3PO_4$ solution. The product was extracted with a $CH_2Cl_2$ (150 ml×2). The extract was dried ($MgSO_4$), and the solvent was distilled off under reduced pressure giving 19 g of solid product. The product was purified by ion exchange chromatography as described in U.S. Pat. No. 5,932,462 giving 14.5 g of 100% pure product.

NMR (d$_6$-DMSO): 1.72 ppm (q, —CH$_2$CH$_2$COO—, 2H) 2.24 ppm (t, —CH$_2$COO—, 2H), 3.12 ppm (q, —CH$_2$NH—, 4H), 3.51 ppm (s, PEG backbone), 3.99 ppm (m, —CH$_2$O(C=O)NH—, 4H), 4.49 ppm (s, —CH$_2$-benzyl), 4H), 7.19 ppm (t, —(C=O)NH—, 2H), 7.33 ppm (m, C$_6$H$_5$—, 10H).

Schematically, the reaction is represented as follows:

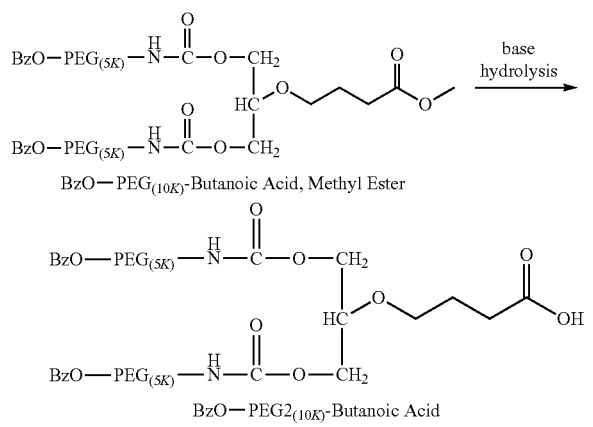

Preparation of BzO-PEG2$_{(10K)}$-Butanoic Acid, N-Hydroxysuccinimide Ester

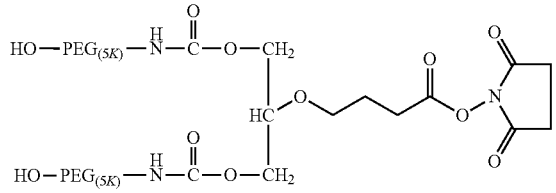

BzO-PEG2$_{(10K)}$-butanoic acid (14.5 g, 0.00145 mole) (prepared as described above) was dissolved in anhydrous dichloromethane (150 ml) and N-hydroxysuccinimide (0.179 g, 0.00156 mole) and 1,3-dicyclocarbodiimide (0.336 g, 0.00163 mole) were added. The mixture was stirred overnight at room temperature under argon atmosphere. Next, part of the solvent was distilled off under reduced pressure and the product was precipitated with isopropyl alcohol at room temperature and dried under vacuum giving 14.0 g of white powder.

NMR (d$_6$-DMSO): 1.81 ppm (q, —CH$_2$CH$_2$COO—, 2H), 2.70 ppm (t, —CH$_2$COO—, 2H), 2.81 ppm (s, —CH$_2$CH$_2$— (succinimide), 4H), 3.12 ppm (q, —CH$_2$NH—, 4H), 3.51 ppm (s, PEG backbone), 3.99 ppm (m, —CH$_2$O(C=O)NH—, 4H), 4.49 ppm (t, —CH$_2$— (benzyl), 4H), 7.22 ppm (t, —(C=O)NH—, 2H), 7.33 ppm (m, C$_6$H$_5$—, 10H).

Preparation of HO-PEG2$_{(10K)}$-Butanoic Acid, N-Hydroxysuccinimide Ester

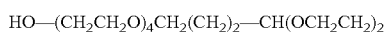

BzO-PEG2$_{(10K)}$-butanoic acid, N-hydroxysuccinimide ester (12.3 g, 0.00123 mole) (prepared as described above) was dissolved in anhydrous ethyl alcohol (240 ml) and palladium hydroxide on the active carbon (20 wt. % of Pd, water content 50%; 0.7 g) was added and the reaction mixture was hydrogenated under 40 psi of hydrogen overnight. Next the mixture was filtered and the solvent was distilled off under reduced pressure. The product was precipitated with isopropyl alcohol at room temperature and dried under vacuum giving 11.5 g of white powder.

NMR (d$_6$-DMSO): 1.81 ppm (q, —CH$_2$CH$_2$COO—, 2H), 2.70 ppm (t, —CH$_2$COO—, 2H), 2.81 ppm (s, —CH$_2$CH$_2$—, succinimide, 4H), 3.12 ppm (q, —CH$_2$NH—, 4H), 3.51 ppm (s, PEG backbone), 3.99 ppm (m, —CH$_2$ONH(C=O), 4H), 4.57 ppm (t, —OH, 2H), 7.22 ppm (t, —(C=O)—NH—, 2H).

Preparation of HO-PEG2$_{(20K)}$-Butyraldehyde, Diethyl Acetal

HO—(CH$_2$CH$_2$O)$_4$CH$_2$(CH$_2$)$_2$—CH(OCH$_2$CH$_2$)$_2$

A mixture of tetra(ethylene glycol) (97.1 g, 0.500 moles) and toluene (200 ml) was azeotropically dried by distilling off toluene under reduced pressure (rotary evaporator). The dried tetra(ethylene glycol) was dissolved in anhydrous toluene (180 ml) and 1.0 M solution of potassium tert-butoxide in tert-butanol (120.0 ml, 0.120 moles) and 4-chlorobutyraldehyde diethyl acetal (18.1 g, 0.100 moles) (Alfa Aesar, Ward Hill, Mass.) were added. The mixture was stirred at 95-100° C. overnight under argon atmosphere. After cooling to room temperature, the mixture was filtered and the solvents were distilled off under reduced pressure. The crude product was dissolved in 1000 ml deionized water and the resulting solution was filtered through active carbon. Sodium chloride (100 g) was added and the product was extracted with dichloromethane (250, 200, and 150 ml). The extract was dried (over MgSO$_4$) and the solvent was distilled off under reduced pressure (by rotary evaporation).

The crude product was dissolved in 300 ml 10% phosphate buffer (pH=7.5) and impurities were extracted with ethyl acetate (2×50 ml). The resulting product was extracted with dichloromethane (200, 150, and 100 ml). The extract was dried (over MgSO$_4$) and the solvent was distilled off under reduced pressure (by rotary evaporation). Yield: 20.3 g.

NMR (d$_6$-DMSO): 1.10 ppm (t, CH$_3$—C—) 1.51 ppm (m, C—CH$_2$—CH$_2$—), 3.49 µm (bm, —OCH$_2$CH$_2$O—), 4.46

NMR (D$_2$O): 1.09 ppm (t, CH$_3$—C—) 1.56 ppm (m, C—CH$_2$—CH$_2$—), 2.69 ppm (t, CH$_2$—N), 3.56 ppm (bm, —OCH$_2$CH$_2$O—), 4.56 ppm (t, —CH, acetal). Purity: ~100%.

HO-PEG2(10 KDa)-butyraldehyde, diethyl acetal

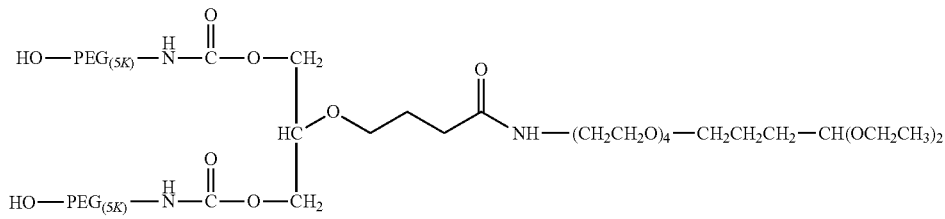

ppm (t, —CH, acetal), 4.58 ppm (t, —OH). Purity: ~100% (no signs of unreacted starting materials).

Preparation of Tetra(ethylene glycol)-α-mesylate-ω-butyraldehyde, diethyl acetal

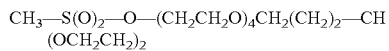

A mixture of tetra(ethylene glycol)mono-butyraldehyde, diethyl acetal (12.5 g, 0.037 moles) and toluene (120 ml) was azeotropically dried by distilling off toluene under reduced pressure (rotary evaporator). The dried tetra(ethylene glycol) mono-butyraldehyde, diethyl acetal was dissolved in anhydrous toluene (100 ml). To the solution was added 20 ml of anhydrous dichloromethane and 5.7 ml of triethylamine (0.041 moles). Then 4.5 g of methanesulfonyl chloride (0.039 moles) was added dropwise. The solution was stirred at room temperature under a nitrogen atmosphere overnight. Next sodium carbonate (5 g) was added, the mixture was stirred for one hour. The solution was then filtered and solvents were distilled off under reduced pressure (rotary evaporator).

NMR (d$_6$-DMSO): 1.10 ppm (t, CH$_3$—C—) 1.51 ppm (m, C—CH$_2$—CH$_2$—), 3.17 ppm (s, CH$_3$-methanesulfonate), 3.49 ppm (bm, —OCH$_2$CH$_2$O—), 4.30 ppm (m, —CH$_2$-methanesulfonate), 4.46 ppm (t, —CH, acetal). Purity: ~100%.

Tetra(ethylene glycol)-α-amino-ω-butyraldehyde, diethyl acetal

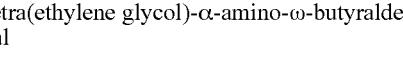

A mixture of tetra(ethylene glycol)-α-mesylate-ω-butyraldehyde, diethyl acetal (14.0 g), concentrated ammonium hydroxide (650 ml), and ethyl alcohol (60 ml) was stirred for 42 hours at room temperature. Next, all volatile materials were distilled off under reduced pressure. The crude product was dissolved in 150 ml deionized water and the pH of the solution was adjusted to 12 with 1.0 M NaOH. The product was extracted with dichloromethane (3×100 ml). The extract was dried (MgSO$_4$) and the solvent was distilled off under reduced pressure (rotary evaporator). Yield 10.6 g.

To a solution of HO-PEG2$_{(10K)}$-butanoic acid, N-hydroxysuccinimide ester (10.6 g, 0.00106 moles) in methylene chloride (100 ml), tetra(ethylene glycol)-α-amino-ω-butyraldehyde, diethyl acetal (0.40 g, 0.00118 moles) and triethylamine (0.037 ml) were added and the reaction mixture was stirred overnight at room temperature under an argon atmosphere. The solvent was evaporated to dryness using a rotary evaporator. The crude product was dissolved in methylene chloride and precipitated with isopropyl alcohol. The wet product was dried under reduced pressure. Yield 10.5 g.

NMR (d$_6$-DMSO): 1.10 ppm (t, CH$_3$CH$_2$—, 6H), 1.51 ppm (m, —CH$_2$CH$_2$-(butyraldehyde), 4H), 1.67 ppm (m, —CH$_2$CH$_2$COO—, 2H), 2.12 ppm (t, —CH$_2$COO—, 2H), 3.12 ppm (q, —CH$_2$NH—, 4H), 3.51 ppm (s, PEG backbone), 3.99 ppm (m, —CH$_2$—O(C=O)—, 4H), 4.46 ppm (t, 1H, acetal). 4.57 ppm (t, —OH, 2H), 7.22 ppm (t, —(C=O)NH—, 2H), 7.82 ppm (t, —(C=O)NH—, 1H). Substitution: ~100%.

BTC-PEG2(10 KDa)-butyraldehyde, diethyl acetal

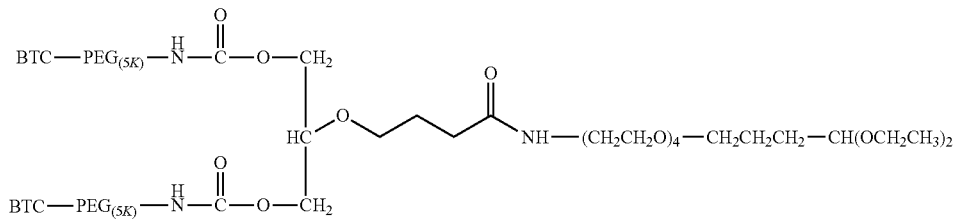

To a solution of HO-PEG2$_{(10K)}$-butyraldehyde, diethyl acetal (10.5 g, 0.00105 moles) in anhydrous acetonitrile (140 ml), pyridine (0.68 ml) and dibenzotriazolyl carbonate (0.89 g of 70% mixture, 0.00210 moles) were added and the reaction mixture was stirred overnight at room temperature under an argon atmosphere. The solvent was evaporated to dryness using a rotary evaporator. The crude product was dissolved in methylene chloride and precipitated with isopropyl alcohol. The wet product was dried under reduced pressure. Yield 10.0 g.

NMR (d$_6$-DMSO): 1.10 ppm (t, CH$_3$CH$_2$—, 6H), 1.51 ppm (m, —CH$_2$CH$_2$-(butyraldehyde), 4H), 1.67 ppm (m, —CH$_2$CH$_2$COO—, 2H), 2.12 ppm (t, —CH$_2$COO—, 2H), 3.12 ppm (q, —CH$_2$NH—, 4H), 3.51 ppm (s, PEG backbone), 3.99 ppm (m, —CH$_2$—O(C=O)—, 4H), 4.46 ppm (t, 1H, acetal), 4.62 ppm (m, PEG-O—CH$_2$—O(C=O)O—, 4H), 7.19 ppm (t, —(C=O)NH—, 2H), 7.41-8.21 ppm (complex mult., benzotriazole protons, 4H), 7.80 ppm (t, —(C=O)NH—, 1H). Substitution: ~100%.

AHPDP-PEG2(10 KDa)-butyraldehyde

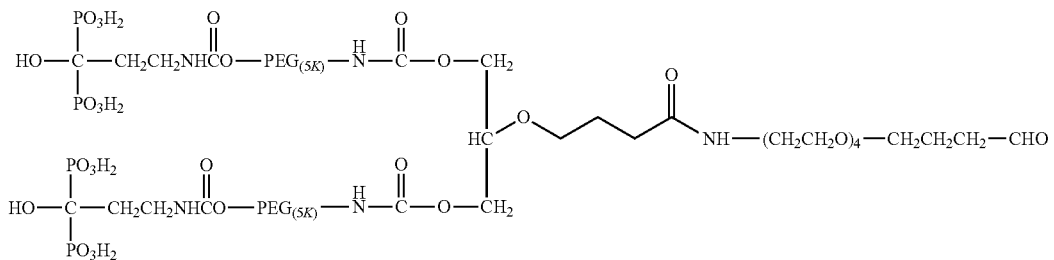

To a solution of BTC-PEG2(10 KDa)-butyraldehyde, diethyl acetal (10 g, 0.0010 moles) in anhydrous methylene chloride (100 ml), 3-amino-1-hydroxypropane-1,1-diphosphonic acid, ditetrabutylammonium salt (AHPDP-2Bu$_4$N) (1.7 g) and triethylamine (3.0 ml) were added and the reaction mixture was stirred overnight at room temperature under argon atmosphere. Next solvent was evaporated to dryness. The crude product was dissolved in DI water (200 ml) and the solution was filtered through Amberlite IR 120 (plus) column (100 ml). Next the pH of the solution was adjusted to 2.5 with a 5% H$_3$PO$_4$. The solution was stirred 3 h then the pH was readjusted to 6.6 with 1M sodium hydroxide. Low molecular weight compounds were removed from the solution by ultrafiltration. Next water was distilled off under reduced pressure giving 6.2 g of white solid product.

NMR (d$_6$-DMSO): 1.75 ppm (m, —CH$_2$—CH$_2$—CHO, 2H and —CH$_2$CH$_2$COO—, 2H), 2.02 ppm (m, —CH$_2$— (AHPDP), 4H), 2.10 ppm (t, —CH$_2$COO—, 2H), 2.44 ppm (dt, —CH$_2$—CHO, 2H), 3.12 ppm (q, —CH$_2$NH—, 4H), 3.51 ppm (s, PEG backbone), 4.03 ppm (m, —CH$_2$—O (C=O)—, 4H), 7.19 ppm (t, —(C=O)—NH—, 2H), 7.80 ppm (t, —(C=O)—NH—, 1H), 9.66 ppm (t, —CHO, 1H).

Example 3

1. Preparation of Trilysine Based BzO-PEG4$_{(20K)}$-Acid

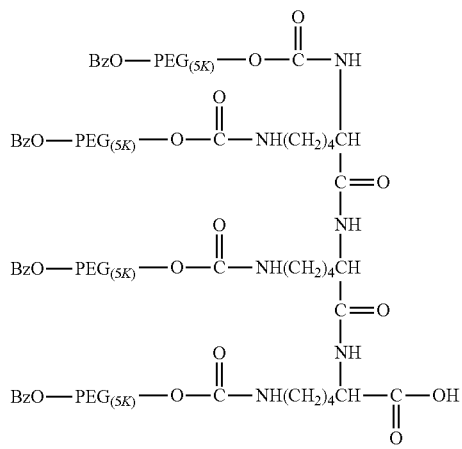

a trilysine based BzO—PEG4(20K)-Acid

Trilysine (1.0 g, 0.00666 equivalents) (Sigma-Aldrich Corporation, St. Louis, Mo.) was dissolved in 0.1M boric acid solution (200 ml) and the pH of the solution was adjusted to 8.5 with 0.1M NaOH. Next Benzyloxy-PEG$_{(5K)}$-benzotriazolyl carbonate (BzO-PEG$_{(5K)}$BTC) (40.0 g, 0.00800 moles) (Nektar Therapeutics, Huntsville, Ala.) was added over 45 min during stirring. During BzO-PEG$_{(5K)}$BTC addition the pH was kept 8.5-9.0 by periodical addition of 0.1M NaOH. Then the reaction mixture was stirred overnight at room temperature. Sodium chloride was added (10 g) and the pH of the mixture was adjusted to 2.0 with 10% solution of H$_3$PO$_4$. The crude product was extracted with CH$_2$Cl$_2$. The extract was dried (MgSO$_4$) and the solvent was distilled off under reduced pressure.

The crude product was purified by ion exchange chromatography as described in U.S. Pat. No. 5,932,462 giving 22.8 g of 100% pure product.

NMR (d$_6$-DMSO): 1.10-175 ppm (complex mult., —CH—(CH$_2$)$_3$-(lysine), 18H), 3.12 ppm (q, —CH$_2$—NH(C=O)—, 6H), 3.51 ppm (s, PEG backbone), 3.92 ppm (m, —CH—COOH, 1H), 4.03 ppm (m, —CH$_2$O(C=O) NH—, 8H), 4.49 ppm (s, —CH$_2$— (benzyl), 8H), 7.14 ppm (t, —CH$_2$NH(C=O)—, 3H), 7.32 ppm (m, —C$_6$H$_5$, 20H and —CHNH(C=O)—, 1H).

2. Trilysine based HO-PEG4$_{(20K)}$-Acid

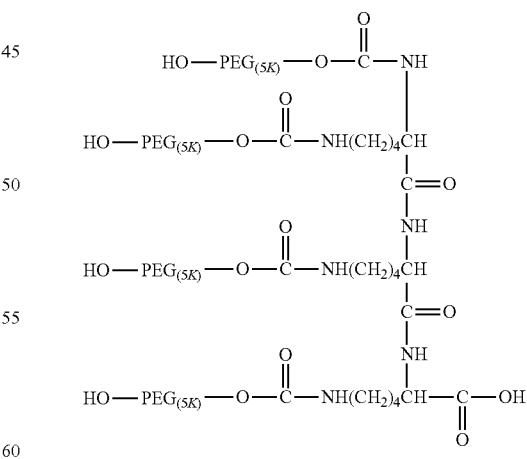

Trilysine based BzO-PEG4$_{(20K)}$ acid (22.0 g, 0.00110 mole) (prepared as described above) was dissolved in ethyl alcohol (96%, 200 ml) and palladium hydroxide on the active carbon (20 wt. % of Pd, water content 50%; 1.5 g) was added and the reaction mixture was hydrogenated under 40 psi of hydrogen overnight. Next the mixture was filtered and the solvent was distilled off under reduced pressure. The crude product was dissolved in $CH_2Cl_2$ (300 ml). The solution was dried ($MgSO_4$) and the solvent was distilled off under reduced pressure. The wet product was dried under vacuum giving 19.5 g of white solid.

NMR ($d_6$-DM1SO): 1.10-175 ppm (complex mult., —CH—(CH$_2$)$_3$— (lysine), 18H), 3.12 ppm (q, —CH$_2$—NH(C=O)—, 6H), 3.51 ppm (s, PEG backbone), 3.92 ppm (m, —CH—COOH, 1H), 4.03 ppm (m, —CH$_2$O(C=O)NH—, 8H), 4.56 ppm (t, —OH, 4H), 7.14 ppm (t, —CH$_2$NH(C=O)—, 3H), 7.31 ppm (d, —CHNH(C=O)—, 1H).

3. Trilysine based HO-PEG4$_{(20K)}$-Butyraldehyde, Diethyl Acetal vent was distilled off under reduced pressure and the product was precipitated with isopropyl alcohol at room temperature and dried under vacuum giving 19.5 g of white powder.

NMR ($d_6$-DMSO): 1.10 ppm (t, CH$_3$CH$_2$—, 6H), 1.10-175 ppm (complex mult., —CH—(CH$_2$)$_3$-(lysine), 18H and —CH$_2$CH$_2$— (butyraldehyde), 4H), 3.12 ppm (q, —CH$_2$—NH(C=O)—, 6H), 3.51 ppm (s, PEG backbone), 3.92 ppm (m, —CH—COO—, 1H), 4.03 ppm (m, —CH$_2$O(C=O)NH—, 8H), 4.46 ppm (t, —CH (acetal), 1H), 4.56 ppm (t, —OH, 4H), 7.14 μm (t, —CH$_2$NH(C=O)—, 3H), 7.31 ppm (d, —CHNH(C=O)—, 1H). Substitution: ~100%.

4. Preparation of trilysine based BTC-PEG4$_{(20K)}$-Butyraldehyde, Diethyl Acetal

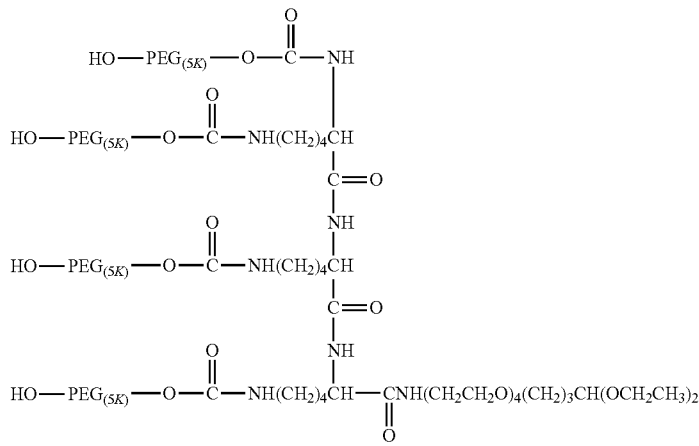

Trilysine based HO-PEG4$_{(20K)}$-Acid (20.0 g, 0.00100 mole) (prepared as described above) was dissolved in anhydrous dichloromethane (200 ml) and tetra(ethylene glycol)-α-amino-ω-butyraldehyde, diethyl acetal (3.70 g, 0.00110 moles) and 1-hydroxybenzotriazole (0.140 g, 0.00105 moles), and N,N-dicyclohexylcarbodiimide (2.30 g, 0.00111 mole) were added. The mixture was stirred overnight at room temperature under argon atmosphere. Next, part of the sol-

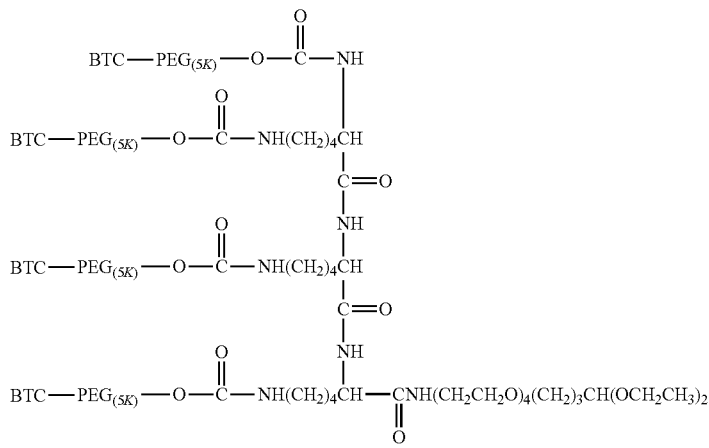

To a solution of trilysine based HO-PEG4$_{(20K)}$-butyraldehyde, diethyl acetal (19.5 g, 0.00390-OH equivalents) in anhydrous acetonitrile (200 ml), pyridine (1.25 ml) and dibenzotriazolyl carbonate (3.30 g of 70% mixture, 0.007800 moles) were added and the reaction mixture was stirred overnight at room temperature under an argon atmosphere. The mixture was filtered and the solvent was evaporated to dryness using a rotary evaporator. The crude product was dissolved in methylene chloride and precipitated with isopropyl alcohol. The wet product was dried under reduced pressure. Yield 19.0 g.

NMR (d$_6$-DMSO): 1.10 ppm (t, C$\underline{H_3}$CH$_2$—, 6H), 1.10-1.75 ppm (complex mult, —CH—(C$\underline{H_2}$)$_3$— (lysine), 18H and —CH$_2$CH$_2$— (butyraldehyde), 4H), 3.12 ppm (q, —C$\underline{H_2}$—NH(C=O)—, 6H), 3.51 ppm (s, PEG backbone), 3.92 ppm (m, —C$\underline{H}$—COO—, 1H), 4.03 ppm (m, —CH$_2$—O (C=O)—, 8H), 4.45 ppm (t, 1H, acetal), 4.62 ppm (m, mPEG-O—CH$_2$—O(C=O)O—, 8H), 7.14 ppm (t, —CH$_2$ N$\underline{H}$(C=O)—, 3H), 7.31 ppm (d, —CHN$\underline{H}$(C=O)—, 1H), 7.41-8.21 ppm (complex mult, benzotriazole protons, 16H). Substitution: ~100%.

5. Preparation of trilysine based AHPDP-PEG2$_{(20K)}$-butyraldehyde

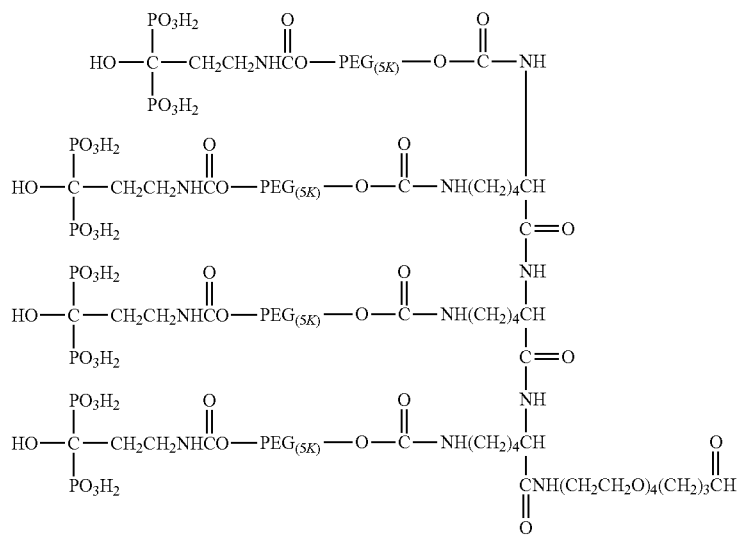

To a solution of trilysine based BTC-PEG4$_{(20K)}$-butyraldehyde, diethyl acetal (19 g, 0.0380-BTC equivalents) in anhydrous methylene chloride (300 ml), 3-amino-1-hydroxypropane-1,1-diphosphonic acid, ditetrabutylammonium salt (AHPDP-2Bu$_4$N) (6.4 g) and triethylamine (5.8 ml) were added and the reaction mixture was stirred overnight at room temperature under argon atmosphere. Next solvent was evaporated to dryness. The crude product was dissolved in DI water (400 ml) and the solution was filtered through Amberlite IR 120 (plus) column (100 ml). Next the pH of the solution was adjusted to 2.5 with a 5% H$_3$PO$_4$. The solution was stirred 3 h then the pH was readjusted to 6.6 with 1M sodium hydroxide. Low molecular weight compounds were removed from the solution by ultrafiltration. Next water was distilled off under reduced pressure giving 17.4 g of white solid product.

NMR (d$_6$-DMSO): 1.10-1.75 ppm (complex mult., —CH—(C$\underline{H_2}$)$_3$— (lysine), 18H), 2.02 ppm (m, —CH$_2$— (AHPDP), 8H), 2.44 ppm (dt, —C$\underline{H_2}$CHO, 2H), 3.12 ppm (q, —C$\underline{H_2}$NH(C=O)—, 4H), 3.51 ppm (s, PEG backbone), 3.92 ppm (m, —C$\underline{H}$—COO—, 1H), 4.03 ppm (m, —CH$_2$—O (C=O)—, 8H), 7.14 ppm (t, 2H), 7.31 ppm (d, 1H), 9.66 ppm (t, —CHO, 1H).

What is claimed is:

1. A polymer conjugate having the structure:

Formula (Ib)

$[Z^3—L^2—(X^2)_a—(POLY^1)_b—(X^1)_c—L^1]_p R—B$ wherein:

B is $—(X^3)_d$-$(L^3)_e$-$(X^4)_f$-POLY$^2$-L$^4$-Drug or $—(X^3)_d$-$(L^3)_e$-$(X^4)_f$-L$^4$-Drug;

each POLY$^1$ and POLY$^2$, which may be the same or different, is a water-soluble, non-peptidic polymer;

each X$^1$, X$^2$, X$^3$, and X$^4$, which may be the same or different, is a spacer moiety;

each L$^1$, L$^2$, L$^3$, and L$^4$ which may be the same or different, are linkages;

Drug is a residue of a biologically active moiety;

Z$^3$ is L$^5$-Drug wherein L$^5$ is a linkage or Z$^3$ is selected from a multiarm structure selected from the group consisting of

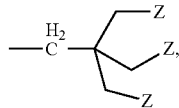

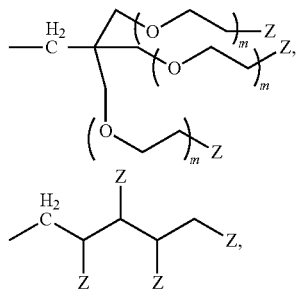

-continued

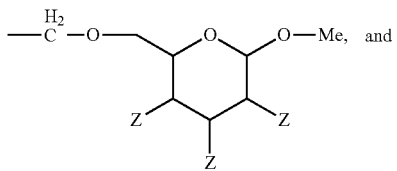

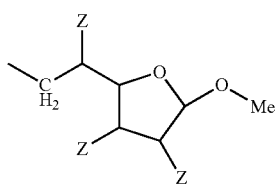

wherein each m is 1-350, Me is methyl, and each Z is a hydroxyapatite-targeting moiety with the proviso that at least one $Z^3$ is a multiarm structure;
  each a, b, c, d, e, and f, which may be the same or different, is either zero or one;
  R is a monomeric or oligomeric multiarm core molecule derived from a molecule comprising at least p+1 sites available for attachment; and
  p is an integer in the range of 2-32.

2. The polymer conjugate of claim 1, wherein each $POLY^1$ and $POLY^2$, when present, has a number average molecular weight of less than about 22,000 Da.

3. The polymer conjugate of claim 2, wherein each $POLY^1$ and $POLY^2$, when present, has a number average molecular weight of less than about 15,000 Da.

4. The polymer conjugate of claim 3, wherein each $POLY^1$ and $POLY^2$, when present, has a number average molecular weight of less than about 8,000 Da.

5. The polymer conjugate of claim 1, wherein each hydroxyapatite-targeting moiety is independently selected from the group consisting of tetracycline, calcein, bisphosphonates, polyaspartic acid, polyglutamic acid, and aminophosphosugars.

6. The polymer conjugate of claim 1, wherein at least one of $L^1$, $L^2$, and $L^3$ is hydrolytically or enzymatically cleavable.

7. The polymer conjugate of claim 1, wherein one or both of $POLY^1$ and $POLY^2$, when present, have a segmented structure comprising two to about five water-soluble, non-peptidic polymer segments attached through linkages.

8. The polymer of claim 7, wherein one or both of $POLY^1$ and $POLY^2$, when present, have a structure according to the formula -POLY-L-POLY-, wherein each POLY is a water-soluble, non-peptidic polymer and L is a linkage.

9. The polymer conjugate of claim 1, wherein each $POLY^1$ and $POLY^2$, when present, are polymers independently selected from the group consisting of poly(alkylene glycols), poly(olefinic alcohol), poly(vinylpyrrolidone), poly(hydroxyalkylmethacrylamide), poly(hydroxyalkylmethacrylate), poly(saccharides), poly(α-hydroxy acid), poly(acrylic acid), poly(vinyl alcohol), polyphosphazene, polyoxazoline, poly(N-acryloylmorpholine), and copolymers, terpolymers, or mixtures thereof.

10. The polymer conjugate of claim 1, wherein each $POLY^1$ and $POLY^2$, when present, is poly(ethylene glycol).

11. The polymer of claim 1, wherein each $POLY^1$ and $POLY^2$, when present, has the structure —$CH_2CH_2O(CH_2CH_2O)_n$—$CH_2CH_2$—, where n is 1-350.

12. The polymer of claim 11, wherein p is 3 to about 10.

13. The polymer of claim 1, wherein R is derived from a polyol with the structure $R^1(OH)_p$, wherein R is a branched hydrocarbon, optionally including one or more ether linkages, and p is at least 3.

14. The polymer of claim 13, wherein the polyol is selected from the group consisting of glycerol, pentaerythritol, and sugar-derived alcohols, and oligomers or polymers of each of the foregoing.

15. The polymer of claim 1, wherein p is 2 to about 10, and R is derived from a molecule selected from the group consisting of polyols, disulfides, and peptides, and oligomers or polymers of each of the foregoing, and combinations thereof.

16. The polymer of claim 1, wherein R is derived from a di-peptide or tri-peptide comprising at least one lysine residue.

17. The polymer conjugate of claim 1, wherein Drug is selected from the group consisting of growth factors, antibiotics, chemotherapeutic agents, and analgesics.

18. The polymer conjugate of claim 17, wherein Drug is a growth factor selected from the group consisting of fibroblast growth factors, platelet-derived growth factors, bone morphogenic proteins, osteogenic proteins, transforming growth factors, LIM mineralization proteins, osteoid-inducing factors, angiogenins, endothelins; growth differentiation factors, ADMP-1, endothelins, hepatocyte growth factor and keratinocyte growth factor, heparin-binding growth factors, hedgehog proteins, interleukins, colony-stimulating factors, epithelial growth factors, insulin-like growth factors, cytokines, osteopontin, and osteonectin.

19. A polymer conjugate comprising the reaction product of the polymer of the formula

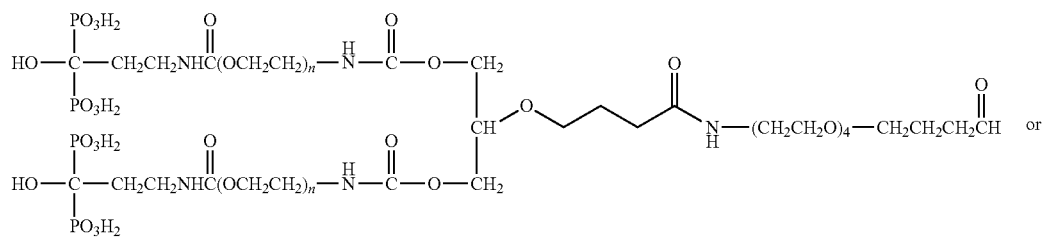

-continued

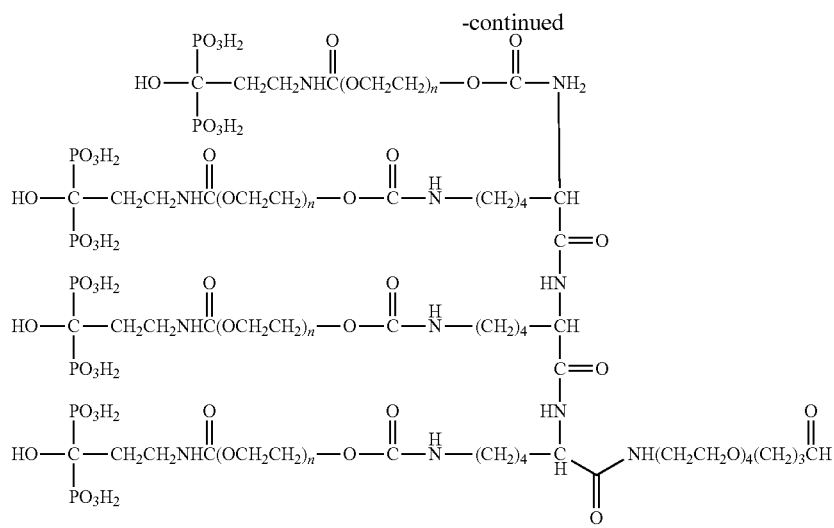

wherein each n is 1-350, with a biologically active agent.

20. The polymer conjugate of claim 19, wherein the biologically active agent is selected from the group consisting of growth factors, antibiotics, chemotherapeutic agents, and analgesics.

21. The polymer conjugate of claim 20, wherein the biologically active agent is a growth factor selected from the group consisting of fibroblast growth factors, platelet-derived growth factors, bone morphogenic proteins, osteogenic proteins, transforming growth factors, LIM mineralization proteins, osteoid-inducing factors, angiogenins, endothelins; growth differentiation factors, ADMP-1, endothelins, hepatocyte growth factor and keratinocyte growth factor, heparin-binding growth factors, hedgehog proteins, interleukins, colony-stimulating factors, epithelial growth factors, insulin-like growth factors, cytokines, osteopontin, and osteonectin.

* * * * *